United States Patent
Yan et al.

(10) Patent No.: US 12,161,706 B2
(45) Date of Patent: Dec. 10, 2024

(54) CANCER VACCINES TARGETING BORIS AND USES THEREOF

(71) Applicant: Inovio Pharmaceuticals, Inc., Plymouth Meeting, PA (US)

(72) Inventors: Jian Yan, Wallingford, PA (US); Anna Slager, Lansdale, PA (US); Bradley Garman, Glenside, PA (US); Neil Cooch, Oreland, PA (US)

(73) Assignee: Inovio Pharmaceuticals, Inc., Plymouth Meeting, PA (US)

( * ) Notice: Subject to any disclaimer, the term of this patent is extended or adjusted under 35 U.S.C. 154(b) by 159 days.

(21) Appl. No.: 17/479,142

(22) Filed: Sep. 20, 2021

(65) Prior Publication Data

US 2021/0401958 A1 Dec. 30, 2021

Related U.S. Application Data

(62) Division of application No. 16/219,268, filed on Dec. 13, 2018, now Pat. No. 11,154,601.

(60) Provisional application No. 62/598,274, filed on Dec. 13, 2017.

(51) Int. Cl.
*A61K 39/00* (2006.01)

(52) U.S. Cl.
CPC ......... *A61K 39/001152* (2018.08); *A61K 39/001184* (2018.08); *A61K 2039/53* (2013.01); *A61K 2039/54* (2013.01); *A61K 2039/572* (2013.01)

(58) Field of Classification Search
CPC ........ A61K 39/001152; A61K 2039/53; A61K 2039/54; A61K 2039/572; A61P 35/00
USPC ...................................................... 424/85.2
See application file for complete search history.

(56) References Cited

U.S. PATENT DOCUMENTS

| | | |
|---|---|---|
| 4,510,245 A | 4/1985 | Cousens et al. |
| 4,554,101 A | 11/1985 | Hopp et al. |
| 4,722,848 A | 2/1988 | Paoletti et al. |
| 4,790,987 A | 12/1988 | Compans et al. |
| 4,797,368 A | 1/1989 | Carter et al. |
| 4,920,209 A | 4/1990 | David et al. |
| 4,945,050 A | 7/1990 | Sanford et al. |
| 5,017,487 A | 5/1991 | Stunnenberg et al. |
| 5,036,006 A | 7/1991 | Sanford et al. |
| 5,077,044 A | 12/1991 | Stocker |
| 5,110,587 A | 5/1992 | Paoletti et al. |
| 5,112,749 A | 5/1992 | Brey et al. |
| 5,174,993 A | 12/1992 | Paoletti |
| 5,223,424 A | 6/1993 | Cochran et al. |
| 5,225,336 A | 7/1993 | Paoletti |
| 5,240,703 A | 8/1993 | Cochran |
| 5,242,829 A | 9/1993 | Panicali et al. |
| 5,273,525 A | 12/1993 | Hofmann |
| 5,294,441 A | 3/1994 | Curtiss et al. |
| 5,294,548 A | 3/1994 | McLinden et al. |
| 5,310,668 A | 5/1994 | Ellis et al. |
| 5,387,744 A | 2/1995 | Curtiss et al. |
| 5,389,368 A | 2/1995 | Roy |
| 5,424,065 A | 6/1995 | Curtiss et al. |
| 5,451,499 A | 9/1995 | Cochran |
| 5,453,364 A | 9/1995 | Paoletti |
| 5,462,734 A | 10/1995 | Letchworth et al. |
| 5,470,734 A | 11/1995 | Sondermeijer et al. |
| 5,474,935 A | 12/1995 | Chatterjee et al. |
| 5,482,713 A | 1/1996 | Paoletti |
| 5,580,859 A | 12/1996 | Felgner et al. |
| 5,591,439 A | 1/1997 | Plotkin et al. |
| 5,593,972 A | 1/1997 | Weiner et al. |
| 5,643,579 A | 7/1997 | Hung et al. |
| 5,650,309 A | 7/1997 | Wong-Staal et al. |
| 5,676,594 A | 10/1997 | Joosten |
| 5,698,202 A | 12/1997 | Ertl et al. |
| 5,703,055 A | 12/1997 | Felgner et al. |
| 5,739,118 A | 4/1998 | Carrano et al. |
| 5,817,637 A | 10/1998 | Weiner et al. |
| 5,827,703 A | 10/1998 | Debs et al. |
| 5,830,876 A | 11/1998 | Weiner et al. |
| 5,955,088 A | 9/1999 | Ghiasi et al. |
| 5,962,428 A | 10/1999 | Carrano et al. |
| 5,981,505 A | 11/1999 | Weiner et al. |
| 6,034,298 A | 3/2000 | Lam et al. |
| 6,042,836 A | 3/2000 | Berman et al. |
| 6,110,161 A | 8/2000 | Mathiesen et al. |
| 6,156,319 A | 12/2000 | Cohen et al. |
| 6,261,281 B1 | 7/2001 | Mathiesen et al. |
| 6,589,529 B1 | 7/2003 | Choi et al. |

(Continued)

FOREIGN PATENT DOCUMENTS

| | | |
|---|---|---|
| CN | 1871025 A | 11/2006 |
| EP | 1667711 B1 | 7/2010 |

(Continued)

OTHER PUBLICATIONS

Database UniProt [Online] Nov. 21, 2017 (Nov. 21, 2017),-: "UniParc-UPI0000E4F4EA", XP055848792.

(Continued)

*Primary Examiner* — Yan Xiao

(74) *Attorney, Agent, or Firm* — BakerHostetler

(57) ABSTRACT

Disclosed herein are nucleic acid molecules comprising one or more nucleic acid sequences that encode a synthetic consensus BORIS antigen. Vectors, compositions, and vaccines comprising one or more nucleic acid sequences that encode a synthetic consensus BORIS antigen are disclosed. Methods of treating a subject with a BORIS-expressing tumor and methods of preventing a BORIS-expressing tumor are disclosed. A synthetic consensus BORIS antigen is disclosed.

3 Claims, 8 Drawing Sheets

Specification includes a Sequence Listing.

(56) References Cited

U.S. PATENT DOCUMENTS

| | | |
|---|---|---|
| 6,697,669 B2 | 2/2004 | Dev et al. |
| 6,939,862 B2 | 9/2005 | Bureau et al. |
| 6,958,060 B2 | 10/2005 | Mathiesen et al. |
| 7,238,522 B2 | 7/2007 | Hebel et al. |
| 7,245,963 B2 | 7/2007 | Draghia-Akli et al. |
| 7,328,064 B2 | 2/2008 | Mathiesen et al. |
| 8,008,265 B2 | 8/2011 | Weiner et al. |
| 8,119,395 B1 | 2/2012 | Weiner et al. |
| 8,173,786 B2 | 5/2012 | Weiner et al. |
| 8,178,660 B2 | 5/2012 | Weiner et al. |
| 9,452,285 B2 | 9/2016 | Draghia-Akli et al. |
| 10,071,154 B2 | 9/2018 | Weiner et al. |
| 2004/0175727 A1 | 9/2004 | Draghia-Akli et al. |
| 2005/0052630 A1 | 3/2005 | Smith et al. |
| 2006/0222629 A1 | 10/2006 | Weiner et al. |
| 2006/0286115 A1 | 12/2006 | Agadjanyan et al. |
| 2007/0048740 A1 | 3/2007 | Isogai et al. |
| 2008/0274140 A1 | 11/2008 | Weiner et al. |
| 2009/0004716 A1 | 1/2009 | Draghia-Akli et al. |
| 2009/0081245 A1 | 3/2009 | Reznik et al. |
| 2012/0244180 A1 | 9/2012 | Weiner et al. |
| 2013/0017224 A1 | 1/2013 | Weiner et al. |
| 2016/0331844 A1 | 11/2016 | Fotin-Mleczek et al. |
| 2017/0298109 A1 | 10/2017 | Torigoe et al. |
| 2022/0111026 A1 | 4/2022 | Yan et al. |

FOREIGN PATENT DOCUMENTS

| | | |
|---|---|---|
| JP | 2007-504154 A | 3/2007 |
| JP | 2018-517674 A | 7/2018 |
| KR | 10-2560562 B1 | 7/2023 |
| RU | 2273645 C2 | 4/2006 |
| RU | 2502800 C2 | 12/2013 |
| WO | 93/24640 A2 | 12/1993 |
| WO | 94/16737 A1 | 8/1994 |
| WO | 98/17799 A1 | 4/1998 |
| WO | 99/43839 A1 | 9/1999 |
| WO | 2005/000235 A2 | 1/2005 |
| WO | 2005/021029 A2 | 3/2005 |
| WO | 2007/050095 A2 | 5/2007 |
| WO | 2007/087178 A2 | 8/2007 |
| WO | 2009/124309 A2 | 10/2009 |
| WO | 2011/032179 A1 | 3/2011 |
| WO | 2011/097640 A1 | 8/2011 |
| WO | 2016/047715 A1 | 3/2016 |
| WO | 2017/136758 A1 | 8/2017 |

OTHER PUBLICATIONS

Ghochikyan A. et al: "Elicitation of T Cell Responses to Histologically Unrelated Tumors by Immunization with the Novel Cancer-Testis Antigen, Brother of the Regulator of Imprinted Sites", The Journal of Immunology, vol. 178, No. 1, Jan. 1, 2007 (Jan. 1, 2007), pp. 566-573, XP055848530.

Mkrtichyan M. et al: "DNA, but not protein vaccine based on mutated BORIS antigen significantly inhibits tumor growth and prolongs the survival of mice", Gene Therapy, Nature Publishing Group, London, GB, vol. 15, No. 1, Jan. 1, 2008 (Jan. 1, 2008), pp. 61-64, XP008090624.

Supplementary European search report Mailed on Oct. 19, 2021 for EP Application No. 18887569.

Mkrtichyan et al.; "Cancer-testis antigen, BORIS based vaccine delivered by dendritic cells is extremely effective against a very aggressive and highly metastatic mouse mammary carcinoma"; Cell Immunol.; vol. 270(2); 2011; p. 188-197.

Okabayashi et al.; "Cancer-testis antigen BORIS is a novel prognostic marker for patients with esophageal cancer"; Cancer Science; vol. 103 No. 9; Sep. 2012; p. 1617-1624.

Mascle et al.; "Point mutations in BCL6 DNA-binding domain reveal distinct roles for the six zinc fingers"; Biochemical 1 and Biophysical Research Comm; vol. 300; 2003; p. 391-396.

Andre et al.; "Increased Immune Response Elicited by DNA Vaccination with a Synthetic gp120 Sequence with Optimized Codon Usage"; Journal of Virology; vol. 72; Feb. 1998; p. 1497-1503.

Baldueva, "Anti Tumor Vaccines", Practical Oncology, vol. 4, No. 3, 2003, pp. 157-166; retrieved from https://rosoncoweb.ru/library/journals/practical oncology/arh015/05.pdf on Oct. 7, 2020 [with machine-generated translation].

Chen et al.; "BORIS, Brother of the Regulator of Imprinted Sites, Is Aberrantly Expressed in Hepatocellular Carcinoma"; Genetic Testing and Molecular Biomarkers; vol. 17; 2013; p. 160-165.

Deml et al.; "Multiple Effects of Codon Usage Optimization on Expression and Immunogenicity of DNA Candidate Vaccines Encoding the Human Immunodeficiency Virus Type 1 Gag Protein"; Journal of Virology; vol. 75; Nov. 2001; p. 10991-110011.

GenBank Accession Identification No. AF336042, May 16, 2002 (online), Retrieved Mar. 1, 2019 from the internet URL: https://www.ncbi.nlm.nih.gov/nuccore/AF336042.1.

International Search Report and Written Opinion issued in PCT/US18/65527, dated Mar. 21, 2019.

Kyte et al.; "A Simple Method for Displaying the Hydropathic Character of a Protein"; J. Mol. Biol.; vol. 157; 1982; p. 105-132.

Link et al.; "BORIS/CTCFL mRNA isoform expression and epigenetic regulation in epithelial ovarian cancer"; Cancer Immunity; vol. 13; Jan. 2013; 9 pages.

Loukinov et al.; "BORIS, a novel male germ-line-specific protein associated with epigenetic reprogramming events, shares the same 11-zinc-finger domain with CTCF, the insulator protein involved in reading imprinting marks in the soma"; PNAS; vol. 99; May 2002; p. 6806-6811.

Muthumani et al.; "Novel engineered HIV-1 East African Clade-A gp160 plasmid construct induces strong humoral and cell-mediated immune responses in vivo"; Virology; vol. 314; Sep. 2003; p. 134-146.

Ohlsson et al.; "CTCF is a uniquely versatile transcription regulator linked to epigenetics and disease"; Trends in Genetics; vol. 17; Sep. 2001; p. 520-527.

Outgoing Written Opinion of the ISA Mailed on Mar. 21, 2019 for WO Application No. PCT/US18/065527.

Schneider et al.; "Inactivation of the Human Immunodeficiency Virus Type 1 Inhibitory Elements Allows Rev-Independent Expression of Gag and Gag/Protease and Particle Formation"; Journal of Virology; vol. 71; Jul. 1997; p. 4892-4903.

Stoll et al.; Structure of the Wilms Tumor Suppressor Protein Zinc Finger Domain Bound DNA; J. Mol. Biol.; vol. 372, 2007; p. 1227-1245.

UniPROT Sequence G3S5Q8_GORGO, Nov. 16, 2011 (online), Retrieved Feb. 26, 2019 from the internet URL: https://www.uniprot.org/uniprot/G3S5Q8.

UniPROT Sequence G3S5Q8_GORGO, Nov. 16, 2011 [online], [Retrieved Feb. 26, 2019]; from the Internet <URL: https:www.uniprot.org/uniprot/G3S5Q8> whole doc.

* denotes mutations to disrupt zinc finger structure and prevent nuclear localization

CANCER VACCINES TARGETING BORIS AND USES THEREOF

CROSS-REFERENCE TO RELATED APPLICATIONS

This application is a divisional of U.S. patent application Ser. No. 16/219,268 filed Dec. 13, 2018, which claims priority to and the benefit of U.S. Provisional Patent Application No. 62/598,274, filed Dec. 13, 2017, the disclosures of which are incorporated herein by reference in their entirety.

SEQUENCE LISTING

This application contains a Sequence Listing which has been submitted electronically in ASCII format and is hereby incorporated by reference in its entirety. Said ASCII copy, created Sep. 17, 2021, is named 104409_000649 sequence_listing_1.txt and is 9,171 bytes in size.

TECHNICAL FIELD

The present invention relates to BORIS antigens and nucleic acid molecules encoding the same. The present invention also relates to vaccines including such BORIS antigens and/or nucleic acid molecules. The present invention further relates to methods of using the vaccines for inducing immune responses and preventing and/or treating subjects having cancer cells and/or tumors that express BORIS.

BACKGROUND

Cancer is among the leading causes of death worldwide. In the United States, cancer is the second most common cause of death, accounting for nearly 1 of every 4 deaths. Cancer arises from a single cell that has transformed from a normal cell into a cancerous cell. Such a transformation is often a multistage process, progressing from a pre-cancerous lesion to malignant tumors. Multiple factors contribute to this progression, including aging, genetic contributions, and exposure to external agents such as physical carcinogens (e.g., ultraviolet and ionizing radiation), chemical carcinogens (e.g., asbestos, components of tobacco smoke, etc.), and biological carcinogens (e.g., certain viruses, bacteria, and parasites).

Prevention, diagnosis, and treatment of cancer may take many different forms. Prevention may include screening for pre-disposing factors (e.g., specific genetic variants), altering behavior (e.g., smoking, diet, and amount of physical activity), and vaccination against viruses (e.g., human papilloma virus hepatitis B virus). Treatment may include chemotherapy, radiation therapy, and surgical removal of a tumor or cancerous tissue. Despite the availability of numerous prevention and treatment methods, such methods often meet with limited success in effectively preventing and/or treating the cancer.

CCCTC-binding factor (CTCF) is an 11-zinc finger factor involved in gene regulation. CTCF's 11 zinc fingers bind varying DNA target sites and act as transcriptional repressors. Brother of the regulator of the imprinted site ("BORIS") or CTCF-like ("CTCFL") is a CTCF paralogue and is also a transcriptional regulator. (Loukinov, D. I. et al. BORIS, a novel male germ-line-specific protein associated with epigenetic reprogramming events, shares the same 11-zinc-finger domain with CTCF, the insulator protein involved in reading imprinting marks in the soma. Proceedings of the National Academy of Sciences of the United States of America 99, 6806-6811, doi:10.1073/pnas.092123699 (2002)). CTCF and BORIS have mutually exclusive expression patterns in normal tissue, but are co-expressed in cancer tissues. Although BORIS mRNA expression is very low or undetectable in normal ovarian tissue, it is highly expressed in many epithelial ovarian carcinoma ("EOC") cells. Aberrant expression of BORIS was detected in 67% of EOC primary tumors. (Link, P. A., et al. BORIS/CTCFL mRNA isoform expression and epigenetic regulation in epithelial ovarian cancer. Cancer Immunity 13, 6 (2013)).

There are 23 distinct BORIS mRNA isoforms generated from alternative splicing, each with canonical exon-intron junctions and poly-A signals, which features are conserved in primates. Six different BORIS isoform families (sf1 through sf6) encode 17 different BORIS proteins. The zinc finger domains of BORIS show homology to those of CTCF; however, dissimilar flanking regions between the two proteins indicate different functional consequences of DNA binding. (See Ohlsson, R., Renkawitz, R. & Lobanenkov, V. CTCF is a uniquely versatile transcription regulator linked to epigenetics and disease. Trends in genetics: TIG 17, 520-527 (2001).) BORIS isoform sf1 is the most differentially expressed among normal ovary and EOC cancer tissue samples.

Vaccines for the treatment and prevention of cancer, and EOC in particular, are of interest. However, existing vaccines targeting tumor cell antigens are limited by poor antigen expression in vivo. Accordingly, a need remains in the art for safe and effective vaccines and methods of their use for preventing and/or treating cancer and reducing mortality in subjects suffering from cancer.

SUMMARY OF THE INVENTION

Provided herein are:

Nucleic acid molecules comprising one or more nucleic acid sequences selected from the group consisting of: (a) a nucleic acid sequence that encodes amino acids 19-680 of SEQ ID NO:2; (b) a nucleic acid sequence that encodes a fragment comprising at least 90% of an entire length of amino acids 19-680 of SEQ ID NO:2; (c) a nucleic acid sequence that encodes a protein that is at least 95% identical to amino acids 19-680 of SEQ ID NO:2; and (d) a nucleic acid sequence that encodes a fragment comprising at least 90% of an entire length of a protein that is at least 95% identical to amino acids 19-680 of SEQ ID NO:2.

Nucleic acid molecules comprising one or more nucleic acid sequences selected from the group consisting of: (a) nucleotides 55-2040 of SEQ ID NO:1; (b) a fragment comprising at least 90% of an entire length of nucleotides 55-2040 of SEQ ID NO:1; (c) a fragment that is at least 95% identical to nucleotides 55-2040 of SEQ ID NO:1; and (d) a fragment comprising at least 90% of an entire length of a nucleic acid sequence that is at least 95% identical to nucleotides 55-2040 of SEQ ID NO:1.

Nucleic acid molecules comprising one or more nucleic acid sequences selected from the group consisting of: (a) a nucleic acid sequence that encodes an entire length of SEQ ID NO:2; (b) a nucleic acid sequence that encodes a fragment comprising at least 90% of an entire length SEQ ID NO:2; (c) a nucleic acid sequence that encodes a protein that is at least 95% identical to SEQ ID NO:2; and (d) a nucleic acid sequence that encodes a fragment comprising at least 90% of an entire length of a protein that is at least 95% identical to SEQ ID NO:2.

Nucleic acid molecules comprising one or more nucleic acid sequences selected from the group consisting of: (a) SEQ ID NO:1; (b) a fragment comprising at least 90% of an entire length of SEQ ID NO:1; (c) a fragment that is at least 95% identical to SEQ ID NO:1; and (d) a fragment comprising at least 90% of an entire length of a nucleic acid sequence that is at least 95% identical to SEQ ID NO:1.

Nucleic acid molecules comprising the nucleic acid sequence set forth in SEQ ID NO:1.

Nucleic acid molecules as described herein for use as a medicament.

Nucleic acid molecules as described herein for use as a medicament in the treatment of cancer.

Nucleic acid molecules as described herein for use in the preparation of a medicament.

Nucleic acid molecules as described herein for use in the preparation of a medicament for the treatment of cancer.

Vectors comprising a nucleic acid molecule as described herein, which vector can be a plasmid or a viral vector.

Compositions comprising one or more nucleic acid molecules as described herein.

Compositions as described herein comprising a pharmaceutically acceptable carrier, which compositions can comprise one or more vectors as described herein.

Proteins comprising the amino acid sequence selected from the group consisting of: (a) amino acids 19-680 of SEQ ID NO:2; (b) a fragment comprising at least 90% of an entire length of amino acids 19-680 of SEQ ID NO:2; (c) an amino acid sequence that is at least 95% identical to amino acids 19-680 of SEQ ID NO:2; and (d) a fragment comprising at least 90% of an entire length of an amino acid sequence that is at least 95% identical to amino acids 19-680 of SEQ ID NO:2.

Proteins comprising the amino acid sequence selected from the group consisting of: (a) SEQ ID NO:2; (b) a fragment comprising at least 90% of an entire length of SEQ ID NO:2; (c) an amino acid sequence that is at least 95% identical to SEQ ID NO:2; and (d) a fragment comprising at least 90% of an entire length of an amino acid sequence that is at least 95% identical to SEQ ID NO:2.

Proteins comprising the amino acid sequence set forth in SEQ ID NO:2.

Vaccines comprising a nucleic acid molecule as described herein.

Vaccines comprising a vector as described herein.

Vaccines as described herein, further comprising a pharmaceutically acceptable excipient, which vaccine can further comprise an adjuvant, wherein the adjuvant can be IL-12, IL-15, IL-28, or RANTES.

Methods of treating a subject with a BORIS-expressing cancerous cell comprising administering a therapeutically effective amount of a vaccine as described herein, wherein administration can include an electroporation step, and wherein administration can occur at one or more sites on the subject.

Methods of vaccinating a subject against a BORIS-expressing cancerous cell comprising administering an amount of a vaccine as described herein effective to induce a humoral or cellular immune response.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In the drawings:

FIG. 7A shows individual animal responses and FIG. 7B shows group responses.

DETAILED DESCRIPTION OF THE INVENTION

Figure 1:
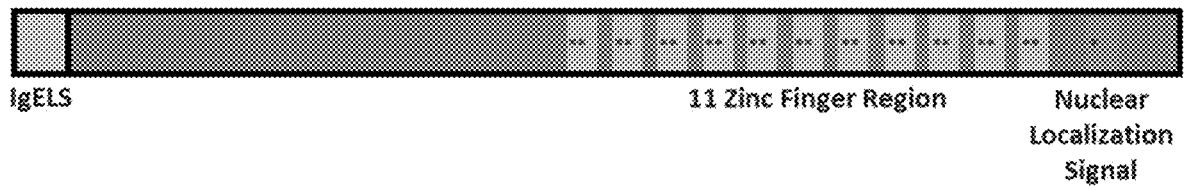
FIG. 1 shows a schematic diagram of the Synthetic consensus BORIS antigen amino acid sequence. Asterisks denote mutations to the 11 zinc finger domains and nuclear localization signal.
Figure 2:
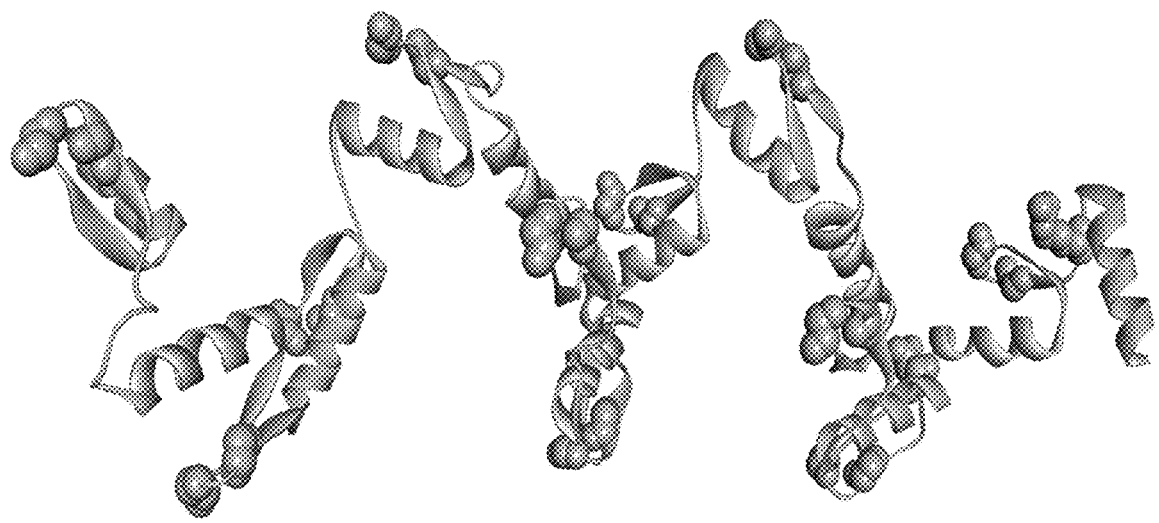
FIG. 2 shows an overall structure of the BORIS protein. Spheres indicate changes relative to native BORIS.
Figure 3:
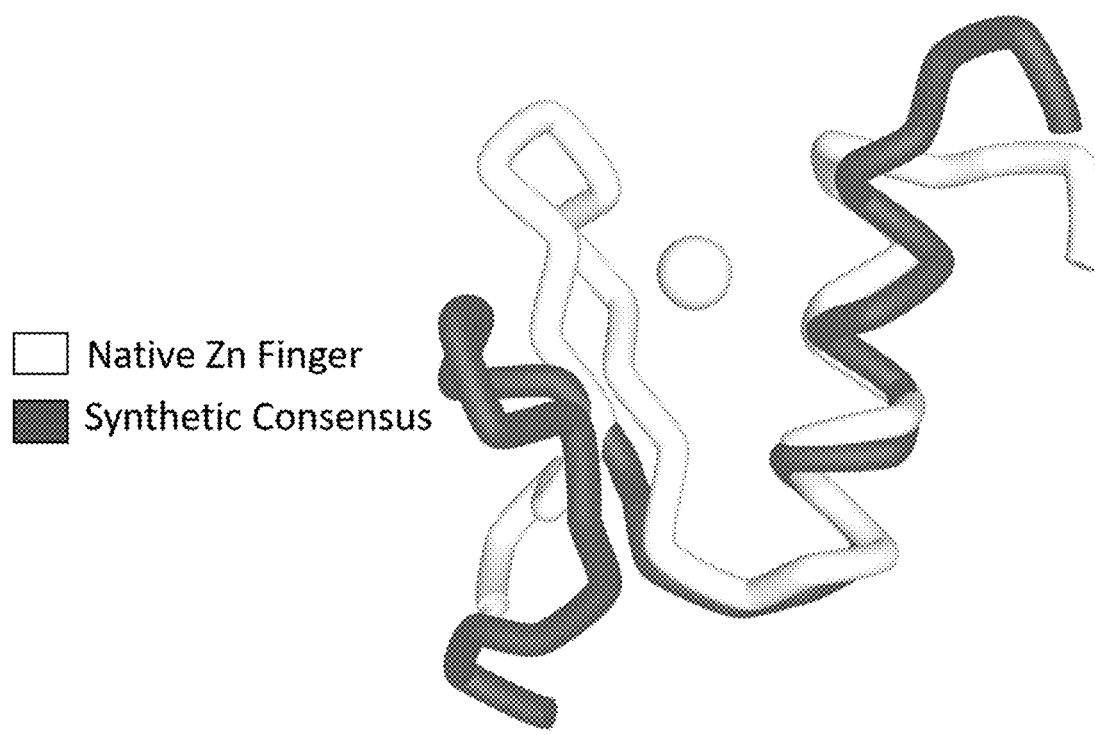
FIG. 3 shows a comparison of native zinc finger to the Synthetic consensus BORIS antigen zinc finger structure. The structure of the Synthetic consensus BORIS antigen zinc finger disrupts DNA binding.

The present invention relates to a vaccine comprising a synthetic consensus BORIS antigen. BORIS is expressed in many tumors. Accordingly, the vaccine provides treatment for a cancer or cancer-based tumors expressing BORIS.

The synthetic consensus BORIS antigen can be a consensus BORIS antigen derived from the sequences of BORIS from different species or from different isoforms within a species, and thus, the synthetic consensus BORIS antigen is non-native. The synthetic consensus BORIS antigen can be further modified by introducing one or more mutations into the consensus sequence to generate the synthetic consensus BORIS antigen sequence. The mutations can interrupt or modify particular functional domains of the native BORIS sequence, thereby disrupting or enhancing the structure or function of the functional domains. In one embodiment, mutations are introduced into the consensus BORIS sequence to disrupt each of the zinc finger domains of native BORIS. In other embodiments of the synthetic consensus BORIS antigen sequence, a mutation is introduced into the nuclear localization signal sequence of native BORIS. In other embodiments, mutations are introduced into the consensus BORIS sequence to disrupt each zinc finger domain and the nuclear localization sequence.

The synthetic consensus BORIS antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α) and/or interleukin 2 (IL-2). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule.

The vaccine of the invention can provide any combination of particular cancer antigens for the particular prevention or treatment of the cancer of a subject that is in need of treatment.

One manner for designing the nucleic acid and its encoded amino acid sequence of the recombinant cancer antigen is by introducing mutations that change particular amino acids in the overall amino acid sequence of the native cancer antigen. The introduction of mutations does not alter the cancer antigen so much that it cannot be universally applied across a mammalian subject, and preferably a human or dog subject, but changes it enough that the resulting amino acid sequence breaks tolerance or is considered a foreign antigen in order to generate an immune response. Another manner may be creating a consensus recombinant cancer antigen that has at least 85% and up to 99% amino acid sequence identity compared to its corresponding native cancer antigen; preferably at least 90% and up to 98% sequence identity; more preferably at least 93% and up to 98% sequence identity; or even more preferably at least 95% and up to 98% sequence identity. In some instances the recombinant cancer antigen has 95%, 96%, 97%, 98%, or 99% amino acid sequence identity compared to its corresponding native cancer antigen. The native cancer antigen is the antigen normally associated with the particular cancer or cancer tumor. Depending upon the cancer antigen, the consensus sequence of the cancer antigen can be across mammalian species or within subtypes of a species or across viral strains or serotypes. Some cancer antigens do not vary greatly from the wild type amino acid sequence of the cancer antigen. Some cancer antigens have nucleic acid/amino acid sequences that are so divergent across species, that a consensus sequence cannot be generated. In these instances, a recombinant cancer antigen that will break tolerance and generate an immune response is generated that has at least 85% and up to 99% amino acid sequence identity compared to its corresponding native cancer antigen; preferably at least 90% and up to 98% sequence identity; more preferably at least 93% and up to 98% sequence identity; or even more preferably at least 95% and up to 98% sequence identity. In some instances the recombinant cancer antigen has 95%, 96%, 97%, 98%, or 99% amino acid sequence identity compared to its corresponding native cancer antigen. The aforementioned approaches can be combined so that the final recombinant cancer antigen has a percent similarity to native cancer antigen amino acid sequence as discussed, above.

The vaccine may be combined further with antibodies to checkpoint inhibitors such as PD-1 and PDL-1 to increase the stimulation of both the cellular and humoral immune responses. Using anti-PD-1 or anti-PDL-1 antibodies prevents PD-1 or PDL-1 from suppressing T-cell and/or B-cell responses. Overall, designing the cancer antigens to be recognized by the immune system helps to overcome other forms of immune suppression by tumor cells, and these vaccines can be used in combination with suppression or inhibition therapies (such as anti-PD-1 and anti-PDL-1 antibody therapies) to further increase T-cell and/or B-cell responses.

The vaccine can increase tumor free survival by 30%, 31%, 32%, 33%, 34%, 35%, 36%, 37%, 38%, 39%, 40%, 41%, 42%, 43%, 44%, and 45%. The vaccine can reduce tumor mass by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% after immunization. The vaccine can prevent and block increases in monocyte chemoattractant protein 1 (MCP-1), a cytokine secreted by myeloid derived suppressor cells. The vaccine can increase tumor survival by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60%.

The vaccine can increase a cellular immune response in a subject administered the vaccine by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the vaccine. In some embodiments the vaccine can increase the cellular immune response in the subject administered the vaccine by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to the cellular immune response in the subject not administered the vaccine.

The vaccine can increase interferon gamma (IFN-γ) levels in a subject administered the vaccine by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to IFN-γ levels in a subject not administered the vaccine. In some embodiments the vaccine can increase IFN-γ levels in the subject administered the vaccine by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to IFN-γ levels in the subject not administered the vaccine.

As described in more detail below, the vaccine can further comprise one or more inhibitors of one or more immune checkpoint molecules (i.e., an immune checkpoint inhibitor). Immune check point molecules are described below in more detail. The immune checkpoint inhibitor is any nucleic acid or protein that prevents the suppression of any component in the immune system such as MEW class presentation, T cell presentation and/or differentiation, B cell presentation and/or differentiation, any cytokine, chemokine or signaling for immune cell proliferation and/or differentiation. As also described below in more detail, the vaccine may be combined further with antibodies to checkpoint inhibitors such as PD-1 and PDL-1 to increase the stimulation of both the cellular and humoral immune responses. Using anti-PD-1 or anti-PDL-1 antibodies prevents PD-1 or PDL-1 from suppressing T-cell and/or B-cell responses.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting. The terminology used herein is for the purpose of describing particular embodiments only and is not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For recitation of numeric ranges herein, each intervening value having the same degree of precision as the recited range minimum and maximum is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Adjuvant" as used herein means any molecule added to the vaccines described herein to enhance the immunogenicity of the antigen.

"Antibody" as used herein means an antibody of class IgG, IgM, IgA, IgD, or IgE, or fragment, or derivative thereof, including Fab, F(ab')2, Fd, and single chain antibodies, diabodies, bispecific antibodies, bifunctional antibodies, and derivatives thereof. The antibody can be an antibody isolated from the serum sample of a mammal, a polyclonal antibody, an affinity purified antibody, or any mixture thereof, which exhibits sufficient binding specificity to a desired epitope or a sequence, derived therefrom.

"Antigen" refers to: proteins having BORIS antigen amino acid sequences including: (a) amino acids 19-680 of SEQ ID NO:2; (b) fragments comprising at least 90% of amino acids 19-680 of SEQ ID NO:2; (c) amino acid sequences that are at least 96% identical to amino acids 19-680 of SEQ ID NO:2; and (d) fragments comprising at least 90% of an amino acid sequence that is at least 96% identical to amino acids 19-680 of SEQ ID NO:2; and proteins having BORIS antigen amino acid sequences including: (a) SEQ ID NO:2; (b) fragments comprising at least 90% of an entire length of SEQ ID NO:2; (c) amino acid sequences that are at least 96% identical to SEQ ID NO:2; and (d) fragments comprising at least 90% of an entire length of an amino acid sequence that is at least 95% identical to SEQ ID NO:2; as well as BORIS antigens comprising the amino acid sequence set forth in SEQ ID NO:2. Antigens may optionally include signal peptides such as those from other proteins.

"Coding sequence" or "encoding nucleic acid" as used herein means the nucleic acids (RNA or DNA molecule) that comprise a nucleotide sequence encoding a protein. The coding sequence can further include initiation and termination signals operably linked to regulatory elements including a promoter and polyadenylation signal capable of directing expression in the cells of a subject or mammal to which the nucleic acid is administered.

"Complement" or "complementary" as used herein with regard to a nucleic acid can mean Watson-Crick (e.g., A-T/U and C-G) or Hoogsteen base pairing between nucleotides or nucleotide analogs of nucleic acid molecules.

"Consensus" or "consensus sequence" or "BORIS consensus sequence" as used herein means a polypeptide sequence based on analysis of an alignment of multiple sequences for the same gene from different organisms or from different isoforms within an organism. Nucleic acid sequences that encode a consensus polypeptide sequence can be prepared.

"Constant current" as used herein describes a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids and vectors, oligonucleotides, siRNA, drugs, ions, and water to pass from one side of the cellular membrane to the other.

"Fragment" as used herein with respect to nucleic acid sequences means a nucleic acid sequence or a portion thereof, that encodes a polypeptide capable of eliciting an immune response in a mammal that cross reacts with an antigen disclosed herein. The fragments can be DNA fragments selected from at least one of the various nucleotide sequences that encode protein fragments set forth below. Fragments can comprise at least 10%, at least 20%, at least 30%, at least 40%, at least 50%, at least 60%, at least 70%, at least 80%, at least 90%, or at least 95% of one or more of the nucleic acid sequences set forth below, excluding an heterologous signal peptide added. The fragment may comprise at least 95%, at least 96%, at least 97%, at least 98%, or at least 99% of one or more of the nucleic acid sequences set forth below and additionally optionally comprise sequence encoding a heterologous signal peptide, which need not be included when calculating percent identity. Fragments may further comprise coding sequences for a signal peptide such as an immunoglobulin signal peptide, for example an IgE or IgG signal peptide. The coding sequence encoding an N terminal methionine and/or signal peptide may be linked to a fragment of coding sequence.

In some embodiments, fragments can comprise at least 20 nucleotides or more, at least 30 nucleotides or more, at least 40 nucleotides or more, at least 50 nucleotides or more, at least 60 nucleotides or more, at least 70 nucleotides or more, at least 80 nucleotides or more, at least 90 nucleotides or more, at least 100 nucleotides or more, at least 150 nucleotides or more, at least 200 nucleotides or more, at least 250 nucleotides or more, at least 300 nucleotides or more, at least 350 nucleotides or more, at least 400 nucleotides or more, at least 450 nucleotides or more, at least 500 nucleotides or more, at least 550 nucleotides or more, at least 600 nucleotides or more, at least 650 nucleotides or more, at least 700 nucleotides or more, at least 750 nucleotides or more, at least 800 nucleotides or more, at least 850 nucleotides or more, at least 900 nucleotides or more, at least 950 nucleotides or more, at least 1000 nucleotides or more, at least 1100 nucleotides or more, at least 1200 nucleotides or more, at least 1300 nucleotides or more, at least 1400 nucleotides or more, at least 1500 nucleotides or more, at least 1600 nucleotides or more, at least 1700 nucleotides or more, at least 1800 nucleotides or more, at least 1900 nucleotides or more, or at least 2000 nucleotides or more of at least one of the nucleic acid sequences set forth below.

"Fragment" or "immunogenic fragment" with respect to polypeptide sequences means a polypeptide capable of eliciting an immune response in a mammal that cross-reacts with an antigen disclosed herein. The fragments can be polypeptide fragments selected from at least one of the various amino acids sequences below. Fragments of consensus proteins can comprise at least 10%, at least 20%, at least 30%, at least 40%, at least 50%, at least 60%, at least 70%, at least 80%, at least 90% or at least 95% of a consensus protein, excluding any heterologous signal peptide added. The fragment may comprise at least 95%, at least 96%, at least 97%, at least 98%, or at least 99% of one or more of the amino sequences set forth below and additionally optionally comprise a heterologous signal peptide, which need not be included when calculating percent identity. Fragments may further comprise a signal peptide such as an immunoglobulin signal peptide, for example an IgE or IgG signal peptide.

In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more, at least 200 amino acids or more, at least 220 amino acids or more, at least 240 amino acids or more, at least 260 amino acids or more, at least 280 amino acids or more, at least 300 amino acids or more, at least 320 amino acids or more, at least 360 amino acids or more, at least 380 amino acids or more, at least 400 amino acids or more, at least 420 amino acids or more, at least 440 amino acids or more, at least 460 amino acids or more, at least 480 amino acids or more, at least 500 amino acids or more, at least 520 amino acids or more, at least 540 amino acids or more, at least 560 amino acids or more, at least 580 amino acids or more, at least 600 amino acids or more, at least 620 amino acids or more, at least 640 amino acids or more, or at least 660 amino acids or more of a protein sequence disclosed herein.

As used herein, the term "genetic construct" refers to the DNA or RNA molecules that comprise a nucleotide sequence that encodes a protein. The coding sequence includes initiation and termination signals operably linked to regulatory elements including a promoter and polyadenylation signal capable of directing expression in the cells of the subject to whom the nucleic acid molecule is administered. As used herein, the term "expressible form" refers to a gene construct that contain the necessary regulatory elements operably linked to a coding sequence that encodes a protein such that, when present in cell of a subject, the coding sequence will be expressed.

The term "homology," as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous," as used herein, refers to a probe that can hybridize to a strand of the double-stranded nucleic acid sequence under conditions of low stringency. When used in reference to a single-stranded nucleic acid sequence, the term "substantially homologous," as used herein, refers to a probe that can hybridize to (i.e., is the complement of) the single-stranded nucleic acid template sequence under conditions of low stringency.

"Identical" or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally derived molecule that is capable of conferring, activating, or enhancing expression of a nucleic acid in a cell. A promoter can comprise one or more specific transcriptional regulatory sequences to further enhance expression and/or to alter the spatial expression and/or temporal expression of a nucleic acid in a cell. A promoter can also comprise distal enhancer or repressor elements, which can be located as much as several thousand base pairs from the start site of transcription. A promoter can be derived from sources including viral, bacterial, fungal, plant, insect, and animal. A promoter can regulate the expression of a gene component constitutively or differentially with respect to cell, tissue, or organ in which expression occurs, or with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the amino terminus (i.e., N terminus) of the protein.

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point (Tm) for the specific sequence at a defined ionic strength pH. The Tm can be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" as used herein can mean a mammal that wants to or is in need of being immunized with the herein described vaccines. The mammal can be a human, chimpanzee, dog, cat, horse, cow, mouse, or rat.

"Substantially complementary" as used herein means that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

"Substantially identical" as used herein means that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

"Treat," "treatment," or "treating" as used herein can mean protecting an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease but before its clinical appearance. Repressing the disease involves administering a vaccine of the present invention to an animal after clinical appearance of the disease.

"Variant" as used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

"Variant" as used herein with respect to a peptide or polypeptide means a peptide or polypeptide that differs in amino acid sequence by the insertion, deletion, or conservative substitution of amino acids, but retains at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome, or yeast artificial chromosome. A vector can be a DNA or RNA vector. A vector can be a self-replicating extrachromosomal vector, and preferably, is a DNA plasmid. The vector can contain or include one or more heterologous nucleic acid sequences.

Vaccines

Provided herein are vaccines comprising a synthetic consensus BORIS antigen as disclosed herein, a nucleic acid molecule encoding a synthetic consensus BORIS antigen, a nucleic acid molecule encoding a fragment of a synthetic consensus BORIS antigen, a nucleic acid molecule encoding a variant of a synthetic consensus BORIS antigen, or combinations thereof. The vaccines can be capable of generating in a subject an immune response against the antigen. The immune response can be a therapeutic or prophylactic immune response. The vaccines may comprise a vector or a plurality of vectors as described in more detail below.

In some embodiments, the vaccine comprises a nucleic acid molecule. In some embodiments, the nucleic acid molecule encodes a synthetic consensus BORIS antigen. In some embodiments, the nucleic acid molecule comprises a nucleic acid sequence that encodes SEQ ID NO: 2; a nucleic acid sequence that encodes a fragment comprising at least 90% of the length of SEQ ID NO 2; a nucleic acid sequence that encodes a protein that is at least 95% identical to SEQ ID NO: 2; or a nucleic acid sequence that encodes a fragment comprising at least 90% of an entire length of a protein that is at least 95% identical to SEQ ID NO: 2. In some embodiments, the nucleic acid molecule comprises SEQ ID NO: 1; a fragment comprising at least 90% of the entire length of SEQ ID NO: 1; a fragment that is at least 95% identical to SEQ ID NO: 1; or a fragment comprising at least 90% of the entire length of a nucleic acid sequence that is at least 95% identical to SEQ ID NO: 1. In some embodiments, the vaccine comprises a synthetic consensus BORIS antigen, wherein the antigen comprises SEQ ID NO: 2; a fragment comprising at least 90% of the length of SEQ ID NO 2; an amino acid sequence that is at least 95% identical to SEQ ID NO: 2; or a fragment comprising at least 90% of an entire length of a protein that is at least 95% identical to SEQ ID NO: 2.

The vaccines can be used to protect against cancer, for example, a cancer or tumor expressing BORIS. The vaccines can be used to prevent and/or treat a tumor expressing BORIS in a subject in need thereof. The vaccines can induce cellular and/or antibody responses against BORIS and against tumors expressing BORIS.

In one embodiment, the vaccines can be used to protect against, to prevent and/or treat, or to induce a cellular and/or antibody response against ovarian cancer cells expressing BORIS, specifically epithelial ovarian cancer cells expressing BORIS, more specifically serous ovarian cancer cells expressing BORIS.

The development of a cancer vaccine as described herein comprises identifying a cancer antigen, e.g., BORIS, that is not recognized by the immune system and is a tumor-associated ("cancer/testis," "C/T") antigen. The cancer antigen identified is changed from a self-antigen to a foreign antigen in order to be recognized by the immune system. The redesign of the nucleic acid and amino acid sequence of the recombinant cancer antigen from a self to a foreign antigen breaks tolerance of the antigen by the immune system. In order to break tolerance, several redesign measures can be applied to the cancer antigen as described below.

The recombinant cancer antigen of the vaccine is not recognized as self, thereby breaking tolerance. The breaking of tolerance can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α) and/or interleukin 2 (IL-2). In other embodiments, the induced or elicited immune response can reduce or inhibit one or more immune suppression factors that promote growth of the tumor or cancer expressing the antigen, for example, but not limited to, factors that downregulate MHC presentation, factors that upregulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule.

In a particular embodiment, the vaccine can mediate clearance or prevent growth of tumor cells by (1) increasing cytotoxic T lymphocyte such as $CD8^+$ and/or $CD107a^+$ (CTL) to attack and kill tumor cells; (2) increasing T helper cell responses; and/or (3) increasing inflammatory responses via IFN-γ, IL-2, and TFN-α, or preferably all of the aforementioned.

The vaccine can be a DNA vaccine. DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome.

The vaccine can include an RNA encoding the cancer antigen. The RNA vaccine can be introduced into the cell.

The vaccine can be an attenuated live vaccine, a vaccine using recombinant vectors to deliver antigen, subunit vaccines, and glycoprotein vaccines, for example, but not limited to, the vaccines described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

In some embodiments, the nucleic acid vaccine may further comprise coding sequence for a molecular adjuvant, in some cases the molecular adjuvant can be IL-12, IL-15, IL-28, IL-31, IL-33, and/or RANTES, and in some cases the molecular adjuvant is a checkpoint inhibitor, including anti-cytotoxic T-lymphocyte antigen 4 (CTLA-4), anti-programmed death receptor-1 (PD-1) and anti-lymphocyte-activation gene (LAG-3). Coding sequence for IL-12, IL-15, IL-28, IL-31, IL-33 and/or RANTES may be included on one or more nucleic acid molecules that comprise coding sequence for one or more antigens. Coding sequence for IL-12, IL-15, IL-28, IL-31, IL-33 and/or RANTES may be included on a separate nucleic acid molecules such as a separate plasmid or vector.

The vaccines of the present invention can have features required of effective vaccines such as being safe so that the vaccine itself does not cause illness or death; being protective against illness; inducing neutralizing antibody; inducing protective T cell responses; and providing ease of administration, few side effects, biological stability, and low cost per dose. The vaccine can accomplish some or all of these features by containing the nucleic acid molecule(s) encoding the cancer antigen as discussed below.

Vaccine in Combination with Immune Checkpoint Inhibitor

The vaccine can further comprise one or more inhibitors of one or more immune checkpoint molecules (i.e., an immune checkpoint inhibitor). Immune check point molecules are described below in more detail. The immune checkpoint inhibitor is any nucleic acid or protein that prevents the suppression of any component in the immune system such as MHC class presentation, T cell presentation and/or differentiation, B cell presentation and/or differentiation, any cytokine, chemokine or signaling for immune cell proliferation and/or differentiation.

Such an inhibitor can be a nucleic acid sequence, an amino acid sequence, a small molecule, or a combination thereof. The nucleic acid sequence can be DNA, RNA, cDNA, a variant thereof, a fragment thereof, or a combination thereof. The nucleic acid can also include additional sequences that encode linker or tag sequences that are linked to the immune checkpoint inhibitor by a peptide bond. The small molecule may be a low molecular weight, for example, less than 800 Daltons, organic or inorganic compound that can serve as an enzyme substrate, ligand (or analog thereof) bound by a protein or nucleic acid, or regulator of a biological process. The amino acid sequence can be protein, a peptide, a variant thereof, a fragment thereof, or a combination thereof.

In some embodiments, the immune checkpoint inhibitor can be one or more nucleic acid sequences encoding an antibody, a variant thereof, a fragment thereof, or a combination thereof. In other embodiments, the immune check point inhibitor can be an antibody, a variant thereof, a fragment thereof, or a combination thereof.

Immune Checkpoint Molecule

The immune check point molecule can be a nucleic acid sequence, an amino acid sequence, a small molecule, or a combination thereof. The nucleic acid sequence can be DNA, RNA, cDNA, a variant thereof, a fragment thereof, or a combination thereof. The nucleic acid can also include additional sequences that encode linker or tag sequences that are linked to the immune checkpoint inhibitor by a peptide bond. The small molecule may be a low molecular weight, for example, less than 800 Daltons, organic or inorganic compound that can serve as an enzyme substrate, ligand (or analog thereof) bound by a protein or nucleic acid, or regulator of a biological process. The amino acid sequence can be protein, a peptide, a variant thereof, a fragment thereof, or a combination thereof.

PD-1 and PD-L1

The immune checkpoint molecule may programmed cell death protein 1 (PD-1), programmed cell death ligand 1 (PD-L1), a fragment thereof, a variant thereof, or a combination thereof. PD-1 is a cell surface protein encoded by the PDCD1 gene. PD-1 is a member of the immunoglobulin superfamily and is expressed on T cells and pro-B cells, and thus, contributes to the fate and/or differentiation of these cells. In particular, PD-1 is a type 1 membrane protein of the CD28/CTLA-4 family of T cell regulators and negatively regulates T cell receptor (TCR) signals, thereby negatively regulating immune responses. PD-1 can negatively regulated CD8+ T cell responses, and thus inhibit CD8-mediated cytotoxicity and enhance tumor growth.

PD-1 has two ligands, PD-L1 and PD-L2, which are members of the B7 family. PD-L1 is upregulated on macrophages and dendritic cells (DCs) in response to LPS and GM-CSF treatment and on T cells and B cells upon TCR and B cell receptor signaling. PD-L1 is expressed by many tumor cell lines, including myelomas, mastocytomas, and melanomas.

Anti-Immune Checkpoint Molecule Antibody

As described above, the immune checkpoint inhibitor can be an antibody. The antibody can bind or react with an antigen (i.e., the immune checkpoint molecule described above.) Accordingly, the antibody may be considered an anti-immune checkpoint molecule antibody or an immune checkpoint molecule antibody. The antibody can be encoded by a nucleic acid sequence contained in The antibody can include a heavy chain polypeptide and a light chain polypeptide. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

The light chain polypeptide can include a variable light chain (VL) region and/or a constant light chain (CL) region. The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

Additionally, the proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites. Accordingly, the antibody can be the Fab or F(ab')$_2$. The Fab can include the heavy chain polypeptide and the light chain polypeptide. The heavy chain polypeptide of the Fab can include the VH region and the CH1 region. The light chain of the Fab can include the VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

PD-1 Antibody

The anti-immune checkpoint molecule antibody can be an anti-PD-1 antibody (also referred to herein as "PD-1 antibody"), a variant thereof, a fragment thereof, or a combination thereof. The PD-1 antibody can be Nivolumab. The anti-PD-1 antibody can inhibit PD-1 activity, thereby inducing, eliciting, or increasing an immune response against a tumor or cancer and decreasing tumor growth.

PD-L1 Antibody

The anti-immune checkpoint molecule antibody can be an anti-PD-L1 antibody (also referred to herein as "PD-L1 antibody"), a variant thereof, a fragment thereof, or a combination thereof. The anti-PD-L1 antibody can inhibit PD-L1 activity, thereby inducing, eliciting, or increasing an immune response against a tumor or cancer and decreasing tumor growth.

Antigens

As described above, the vaccine can comprise an antigen or a nucleic acid encoding an antigen. The antigen can be BORIS, a fragment thereof, a variant thereof, or a combination of a fragment and a variant thereof.

Accordingly, the vaccine can be used for treating subjects suffering from cancers or tumors that express BORIS. In some embodiments, the cancer is ovarian cancer. In some embodiments the ovarian cancer is epithelial ovarian cancer. The ovarian cancer may be serous epithelial ovarian cancer. The vaccine can also be used for treating subjects with cancers or tumors that express BORIS for preventing development of such tumors in subjects. The synthetic consensus BORIS antigen can differ from the native BORIS gene, and thus provide therapy or prophylaxis against a BORIS antigen-expressing tumor. Accordingly, synthetic consensus BORIS antigen sequences that differ from the native BORIS gene (i.e., mutated or synthetic BORIS genes or sequences) are provided herein.

Transcripts of the native BORIS gene are processed into a variety of mRNAs. Particular BORIS mRNA isoforms can be selected based, for example, on their expression in cancer cells. In particular embodiments, the BORIS isoform is selected based on its expression in ovarian cancer cells. The synthetic consensus BORIS antigen sequences described herein avoid alternative processing, producing one full-length transcript and resulting in stronger induction of effector T and B cell responses.

Isolated nucleic acid molecules comprising the above-described heterologous sequences are provided. Isolated nucleic acid molecules consisting of the above-described heterologous sequences are provided. Isolated nucleic acid molecules comprising the above-described heterologous sequences may be incorporated into vectors such as plasmids, viral vectors and other forms of nucleic acid molecules as described below. Provided herein are nucleic acid sequences that encode synthetic consensus BORIS antigens. Coding sequences encoding synthetic consensus BORIS antigens have the sequences as described above.

Protein molecules comprising the above-described heterologous synthetic consensus BORIS antigen amino acid sequences are provided. Protein molecules consisting of the above-described heterologous synthetic consensus BORIS antigen amino acid sequences are provided. Provided herein are proteins and polypeptides having the above-described synthetic consensus BORIS antigen sequences. The proteins and polypeptide may be referred to as synthetic consensus BORIS antigens and BORIS immunogens. Synthetic consensus BORIS antigens are capable of eliciting an immune response against tumors expressing BORIS.

In one aspect, it is desired that the synthetic consensus BORIS antigen provide for improved transcription and translation, including having one or more of the following: low GC content leader sequence to increase transcription; mRNA stability and codon optimization; and, to the extent possible, elimination of cis-acting sequence motifs (i.e., internal TATA-boxes).

The synthetic consensus BORIS antigen can be a consensus antigen (or immunogen) sequence derived from two or more species. In one embodiment, a consensus sequence is generated from BORIS isoforms of different species. The consensus sequence is derived from BORIS sequences collected from GenBank or other similar DNA or protein sequence database. The synthetic consensus BORIS antigen can comprise a consensus sequence and/or modification(s) for improved expression. Modification can include codon optimization, RNA optimization, addition of a kozak sequence (e.g., GCC ACC) for increased translation initiation and/or the addition of an immunoglobulin leader sequence to increase the immunogenicity of the synthetic consensus BORIS antigen. The synthetic consensus BORIS antigen can comprise a signal peptide such as an immunoglobulin signal peptide, for example, but not limited to, an immunoglobulin E (IgE) or immunoglobulin G (IgG) signal peptide. In some embodiments, the BORIS consensus antigen can comprise a hemagglutinin (HA) tag. The BORIS consensus antigen can be designed to elicit stronger and broader cellular and/or humoral immune responses than a corresponding codon optimized synthetic consensus BORIS antigen.

The consensus BORIS sequence can be mutated to disrupt and/or to enhance particular structures and/or functions of native BORIS to produce a synthetic consensus BORIS antigen sequence. In one embodiment, mutations are introduced into each of 11 zinc finger domains to disrupt zinc finger structure and functionality. The one or more mutations can be a substitution of one or more of the amino acids that coordinate the zinc ion in the one or more zinc fingers. The one or more amino acids that coordinate the zinc ion can be a CCHH motif. Accordingly, in some embodiments, the one or more mutations can replace 1, 2, 3, or all 4 amino acids of one or more CCHH motif. In a preferred embodiment, the cysteines in the eleven zinc fingers in BORIS are mutated to glycines to disrupt zinc finger structure and binding. (See Stoll, R. et al. Structure of the Wilms tumor suppressor protein zinc finger domain bound to DNA. Journal of molecular biology 372, 1227-1245, doi:10.1016/j.jmb.2007.07.017 (2007)).

The synthetic consensus BORIS antigen can comprise mutations or deletions to disrupt, e.g., a native localization signal sequence including, for example, a nuclear localization signal to disrupt nuclear translocation upon expression. For example, RRRK can be substituted for RKRK to prevent nuclear localization. In a particular embodiment, disruptions are made to each of the 11 zinc finger domains and to the nuclear localization signal sequence. It will be readily appreciated by persons of skill in the art that a recombinant synthetic consensus BORIS antigen having one or more, or any combination of, the mutations herein described will likewise have functionality as a non-self-antigen for purposes of this disclosure, and that each of these variants is contemplated by the present disclosure.

In a preferred embodiment, the synthetic consensus BORIS antigen sequence shares 95.0% identity with SEQ ID NO:1. In this embodiment, the nucleic acid sequence of SEQ ID NO:1 encodes an amino acid sequence of SEQ ID NO:2. In other embodiments, the synthetic consensus BORIS antigen sequence shares 95.0% or more identity, 95.2% or more identity, 95.4% or more identity, 95.6% or more identity, 95.8% or more identity, 96.0% or more identity, 96.2% or more identity, 96.4% or more identity, 96.6% or more identity, 96.8% or more identity, 97.0% or more identity, 97.2% or more identity, 97.4% or more identity, 97.6% or more identity, 97.8% or more identity, 98.0% or more identity, 98.2% or more identity, 98.4% or more identity, or 98.6% or more identity, 98.8% or more identity, 99.0% or more identity, 99.2% or more identity, 99.4% or more identity, 99.6% or more identity, 99.8% or more identity, or 100% identity with SEQ ID NO:1.

Vectors

The vaccine can comprise one or more vectors that include a heterologous nucleic acid encoding the synthetic consensus BORIS antigen. For example, the one or more vectors can include a nucleic acid sequence encoding an entire length of the amino acid sequence of SEQ ID NO: 2; a nucleic acid sequence encoding a fragment comprising at least 90% of an entire length SEQ ID NO:2; a nucleic acid sequence encoding a protein that is at least 95% identical to SEQ ID NO:2; or a nucleic acid sequence encoding a fragment comprising at least 90% of an entire length of a protein that is at least 95% identical to SEQ ID NO:2. The one or more vectors can include a nucleic acid sequence encoding amino acids 19-680 of SEQ ID NO: 2; a nucleic acid sequence encoding a fragment comprising at least 90% of an entire length of amino acids 19-680 of SEQ ID NO:2; a nucleic acid sequence encoding a protein that is at least 95% identical to amino acids 19-680 of SEQ ID NO:2; or a nucleic acid sequence that encodes a fragment comprising at least 90% of an entire length of a protein that is at least 95% identical to amino acids 19-680 of SEQ ID NO:2. The one or more vectors can be capable of expressing the synthetic consensus BORIS antigen in a quantity effective to elicit an immune response in the mammal. The vector may comprise heterologous nucleic acid encoding the synthetic consensus BORIS antigen. The vector can have a nucleic acid sequence containing an origin of replication. The vector can be a plasmid, bacteriophage, bacterial artificial chromosome or yeast artificial chromosome. The vector can be either a self-replication extra chromosomal vector, or a vector that integrates into a host genome.

The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

The vector can be a circular plasmid or a linear nucleic acid. The circular plasmid and linear nucleic acid are capable of directing expression of a particular nucleotide sequence in an appropriate subject cell. The vector can have a promoter operably linked to the antigen-encoding nucleotide sequence, which may be operably linked to termination signals. The vector can also contain sequences required for proper translation of the nucleotide sequence as well as sequences for cloning and subcloning the vector and fragments thereof. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development. In a preferred embodiment, the plasmid vector is pGX1440 described herein, further comprising the nucleic acid sequence of SEQ ID NO:1.

The vector can be a plasmid. The plasmid may be useful for transfecting cells with nucleic acid encoding the antigen. The transformed host cells can be cultured and maintained under conditions wherein expression of the antigen takes place.

The plasmid may comprise a nucleic acid sequence that encodes one or more of the various antigens disclosed above including coding sequences that encode synthetic, consensus antigen capable of eliciting an immune response against an antigen, fragments of such proteins, variants of such proteins, fragments of variants or fusion proteins which are made up of combinations of consensus proteins and/or fragments of consensus protein and/or variants of consensus protein and/or fragments of variants of consensus proteins.

A single plasmid may contain coding sequence for a single antigen, coding sequence for two antigens, coding sequence for three antigens or coding sequence for four antigens.

In some embodiments, a plasmid may further comprise coding sequence that encodes CCR20 alone or as part of one these plasmids. Similarly, plasmids may further comprise coding sequences for IL-12, IL-15 and/or IL-28.

The plasmid may further comprise an initiation codon, which may be upstream of the coding sequence, and a stop codon, which may be downstream of the coding sequence. The initiation and termination codon may be in frame with the coding sequence.

The plasmid may also comprise a promoter that is operably linked to the coding sequence. The promoter operably linked to the coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, or human metallothionein. The promoter may also be a tissue specific promoter, such as a muscle or skin specific promoter, natural or synthetic. Examples of such promoters are described in US patent application publication no. US20040175727, the contents of which are incorporated herein in its entirety.

The plasmid may also comprise a polyadenylation signal, which may be downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, CA).

The plasmid may also comprise an enhancer upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

The plasmid may also comprise a mammalian origin of replication in order to maintain the plasmid extrachromosomally and produce multiple copies of the plasmid in a cell. The plasmid may be pVAXI, pCEP4 or pREP4 from Invitrogen (San Diego, CA), which may comprise the Epstein Barr virus origin of replication and nuclear antigen EBNA-1 coding region, which may produce high copy episomal replication without integration. The backbone of the plasmid may be pA V0242. The plasmid may be a replication defective adenovirus type 5 (Ad5) plasmid.

The plasmid may also comprise a regulatory sequence, which may be well suited for gene expression in a cell into which the plasmid is administered. The coding sequence may comprise a codon that may allow more efficient transcription of the coding sequence in the host cell.

The coding sequence may also comprise an Ig leader sequence. The leader sequence may be 5' of the coding sequence. The consensus antigens encoded by this sequence may comprise an N-terminal Ig leader followed by a consensus antigen protein. The N-terminal Ig leader may be IgE or IgG.

The plasmid may be pSE420 (Invitrogen, San Diego, Calif.), which may be used for protein production in *Escherichia coli* (*E. coli*). The plasmid may also be p YES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNA I or pcDNA3 (Invitrogen, San Diego, Calif.), which may be used for protein production in mammalian cells such as Chinese hamster ovary (CHO) cells.

The vector may be circular plasmid, which may transform a target cell by integration into the cellular genome or exist extrachromosomally (e.g., autonomous replicating plasmid with an origin of replication).

The vector can be pVAX, pcDNA3.0, or provax, or any other expression vector capable of expressing DNA encoding the antigen and enabling a cell to translate the sequence to an antigen that is recognized by the immune system.

Also provided herein is a linear nucleic acid vaccine, or linear expression cassette ("LEC"), that is capable of being efficiently delivered to a subject via electroporation and expressing one or more desired antigens. The LEC may be any linear DNA devoid of any phosphate backbone. The DNA may encode one or more antigens. The LEC may contain a promoter, an intron, a stop codon, and/or a polyadenylation signal. The expression of the antigen may be controlled by the promoter. The LEC may not contain any antibiotic resistance genes and/or a phosphate backbone. The LEC may not contain other nucleic acid sequences unrelated to the desired antigen gene expression.

The LEC may be derived from any plasmid capable of being linearized. The plasmid may be capable of expressing the antigen. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen and enabling a cell to translate the sequence to an antigen that is recognized by the immune system.

The LEC can be perM2. The LEC can be perNP. perNP and perMR can be derived from pNP (Puerto Rico/34) and pM2 (New Caledonia/99), respectively.

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleic acid sequence encoding the antigen and signals required for efficient polyadenylation of the transcript, ribosome binding sites, and translation termination.

The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

Methods of Preparing the Vector

Provided herein are methods for preparing vectors that comprise the DNA vaccines discussed herein. The vectors, after the final subcloning step, can be used to inoculate a cell culture in a large-scale fermentation tank, using known methods in the art.

The vector for use with the EP devices, which are described below in more detail, can be formulated or manufactured using a combination of known devices and techniques, but preferably they are manufactured using an optimized manufacturing technique that is described in co-pending U.S. provisional application U.S. Ser. No. 60/939,792, which was filed on May 23, 2007 (see U.S. Pat. Pub. No. 20090004716). In some examples, the DNA vectors used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

Excipients and Other Components of the Vaccine

The vaccine may further comprise a pharmaceutically acceptable excipient. The pharmaceutically acceptable excipient can be a functional molecule such as a vehicle, carrier, or diluent. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection-facilitating agent is a polyanion, polycation, including poly-L-glutamate (LGS), or lipid. The transfection-facilitating agent is poly-L-glutamate, and the poly-L-glutamate may be present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. The DNA vector vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection-facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be one or more adjuvants. The adjuvant can be other genes that are expressed in an alternative plasmid or vector, or are delivered as proteins in combination with the plasmid or vector above in the vaccine. The one or more adjuvants may be selected from the group consisting of: CCL20, α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, IL-28, MHC, CD80, CD86, IL-1, IL-2, IL-4, IL-5, IL-6, IL-10, IL-18, IL-33, MCP-1, MIP-la, MIP-1~, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DRS, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-I, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAPI, TAP2, IL-15 having the signal sequence or coding sequence that encodes the signal sequence deleted and optionally including a different signal peptide such as that from IgE or coding sequence that encodes a different signal peptide such as that from IgE, and functional fragments thereof, or a combination thereof. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

In some embodiments, the adjuvant may be one or more nucleic acid molecules that encode proteins selected from the group consisting of: CCL-20, IL-12, IL-15, IL-28, CTACK, TECK, MEC or RANTES. Examples of IL-12 constructs and sequences are disclosed in PCT application no. PCT/US1997/019502 and corresponding U.S. application Ser. No. 08/956,865, and U.S. Provisional Application Ser. No. 61/569,600 filed Dec. 12, 2011, which are each incorporated herein by reference. Examples of IL-15 constructs and sequences are disclosed in PCT application no. PCT/US04/18962 and corresponding U.S. application Ser. No. 10/560,650, and in PCT application no. PCT/US07/00886 and corresponding U.S. application Ser. No. 12/160,766, and in PCT application no. PCT/USI0/048827, which are each incorporated herein by reference. Examples of iL-28 constructs and sequences are disclosed in PCT application no. PCT/US09/039648 and corresponding U.S. application Ser. No. 12/936,192, which are each incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of chemokines CTACK, TECK and MEC constructs and sequences are disclosed in PCT application no. PCT/US2005/042231 and corresponding U.S. application Ser. No. 11/719,646, which are each incorporated herein by reference. Examples of OX40 and other immunomodulators are disclosed in U.S. application Ser. No. 10/560,653, which is incorporated herein by reference. Examples of DR5 and other immunomodulators are disclosed in U.S. application Ser. No. 09/622,452, which is incorporated herein by reference.

Other genes that can be useful as adjuvants include those encoding: MCP-1, MIP-la, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine may further comprise a genetic vaccine facilitator agent as described in U.S. Ser. No. 021,579 filed Apr. 1, 1994, which is fully incorporated by reference.

The vaccine may comprise the antigen-encoding vector at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, vaccine according to the present invention comprise about 5 nanogram to about 1000 micrograms of DNA. In some preferred embodiments, vaccine can contain about 10 nanograms to about 800 micrograms of DNA. In some preferred embodiments, the vaccine can contain about 0.1 to about 500 micrograms of DNA. In some preferred embodiments, the vaccine can contain about 1 to about 350 micrograms of DNA. In some preferred embodiments, the vaccine can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the antigen or plasmid encoding the same.

The vaccine can be formulated according to the mode of administration to be used. An injectable vaccine pharmaceutical composition can be sterile, pyrogen free and particulate free. An isotonic formulation or solution can be used. Additives for isotonicity can include sodium chloride, dextrose, mannitol, sorbitol, and lactose. The vaccine can comprise a vasoconstriction agent. The isotonic solutions can include phosphate buffered saline. Vaccine can further comprise stabilizers including gelatin and albumin. The stabilizers can allow the formulation to be stable at room or ambient temperature for extended periods of time, including LGS or polycations or polyanions.

Pharmaceutical Compositions of the Vaccine

The vaccine can be in the form of a pharmaceutical composition. The pharmaceutical composition can comprise the vaccine. The pharmaceutical compositions can comprise about 5 nanograms (ng) to about 10 milligrams (mg) of the nucleic acid molecule(s) of the vaccine. In some embodiments, pharmaceutical compositions according to the present invention comprise about 25 ng to about 5 mg the nucleic acid molecule(s) of the vaccine. In some embodiments, the pharmaceutical compositions contain about 50 ng to about 1 mg the nucleic acid molecule(s) of the vaccine. In some embodiments, the pharmaceutical compositions contain about 0.1 to about 500 micrograms of the nucleic acid molecule(s) of the vaccine. In some embodiments, the pharmaceutical compositions contain about 1 to about 350 micrograms of the nucleic acid molecule(s) of the vaccine. In some embodiments, the pharmaceutical compositions contain about 5 to about 250 micrograms of the nucleic acid molecule(s) of the vaccine. In some embodiments, the pharmaceutical compositions contain about 10 to about 200 micrograms of the nucleic acid molecule(s) of the vaccine. In some embodiments, the pharmaceutical compositions contain about 15 to about 150 micrograms of the nucleic acid molecule(s) of the vaccine. In some embodiments, the pharmaceutical compositions contain about 20 to about 100 micrograms of the nucleic acid molecule(s) of the vaccine. In some embodiments, the pharmaceutical compositions contain about 25 to about 75 micrograms of the nucleic acid molecule(s) of the vaccine. In some embodiments, the pharmaceutical compositions contain about 30 to about 50 micrograms of the nucleic acid molecule(s) of the vaccine. In some embodiments, the pharmaceutical compositions contain about 35 to about 40 micrograms of the nucleic acid molecule(s) of the vaccine. In some embodiments, the pharmaceutical compositions contain about 100 to about 200 micrograms of the nucleic acid molecule(s) of the vaccine. In some embodiments, the pharmaceutical compositions comprise about 10 micrograms to about 100 micrograms of the nucleic acid molecule(s) of the vaccine. In some embodiments, the pharmaceutical compositions comprise about 20 micrograms to about 80 micrograms of the nucleic acid molecule(s) of the vaccine. In some embodiments, the pharmaceutical compositions comprise about 25 micrograms to about 60 micrograms of the nucleic acid molecule(s) of the vaccine. In some embodiments, the pharmaceutical compositions comprise about 30 ng to about 50 micrograms of the nucleic acid molecule(s) of the vaccine. In some embodiments, the pharmaceutical compositions comprise about 35 ng to about 45 micrograms of the nucleic acid molecule(s) of the vaccine. In some preferred embodiments, the pharmaceutical compositions contain about 0.1 to about 500 micrograms of the nucleic acid molecule(s) of the vaccine. In some preferred embodiments, the pharmaceutical compositions contain about 1 to about 350 micrograms of the nucleic acid molecule(s) of the vaccine. In some preferred embodiments, the pharmaceutical compositions contain about 25 to about 250 micrograms of the nucleic acid molecule(s) of the vaccine. In some preferred embodiments, the pharmaceutical compositions contain about 100 to about 200 micrograms of the nucleic acid molecule(s) of the vaccine.

In some embodiments, pharmaceutical compositions according to the present invention comprise at least 10, 15, 20, 25, 30, 35, 40, 45, 50, 55, 60, 65, 70, 75, 80, 85, 90, 95 or 100 ng the nucleic acid molecule(s) of the vaccine. In some embodiments, the pharmaceutical compositions can comprise at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms of the nucleic acid molecule(s) of the vaccine. In some embodiments, the pharmaceutical composition can comprise at least 1.5, 2, 2.5, 3, 3.5, 4, 4.5, 5, 5.5, 6, 6.5, 7, 7.5, 8, 8.5, 9, 9.5 or 10 mg or more the nucleic acid molecule(s) of the vaccine.

In other embodiments, the pharmaceutical composition can comprise up to and including 15, 20, 25, 30, 35, 40, 45, 50, 55, 60, 65, 70, 75, 80, 85, 90, 95 or 100 ng the nucleic acid molecule(s) of the vaccine. In some embodiments, the pharmaceutical composition can comprise up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms of the nucleic acid molecule(s) of the vaccine. In some embodiments, the pharmaceutical composition can comprise up to and including 1.5, 2, 2.5, 3, 3.5, 4, 4.5, 5, 5.5, 6, 6.5, 7, 7.5, 8, 8.5, 9, 9.5 or 10 mg the nucleic acid molecule(s) of the vaccine.

The pharmaceutical composition can further comprise other agents for formulation purposes according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The pharmaceutical composition can further comprise a pharmaceutically acceptable excipient as provided above in Section 2. For example, the pharmaceutically acceptable excipient can comprise the functional molecules, vehicles, adjuvants, carriers, diluents, or transfection facilitating agents, as provided in Section 2.

Indications

The vaccines and the pharmaceutical compositions comprising the vaccines provided herein can be used in the treatment or prevention of cancer cells and cancer-based tumors expressing BORIS. In particular, the vaccines and the pharmaceutical compositions comprising the vaccines provided herein can be used in the treatment or prevention of ovarian cancer, more particularly epithelial ovarian cancer, most particularly serous ovarian cancer.

Methods of Vaccination

Provided herein are methods for treating and/or preventing cancer using the pharmaceutical formulations described above. Also described herein are methods of using the pharmaceutical formulations described above in the treatment and/or prevention of cancer in a subject. Also described herein are methods of vaccinating a subject. Also described herein are methods of administering the pharmaceutical formulations described herein to a subject in need thereof. The methods described herein collectively referred to as methods of treatment using the pharmaceutical formulations described herein can comprise administering one or more vaccine as described herein to a subject in need thereof to induce a therapeutic and/or prophylactic immune response. The vaccine can be administered to a subject to modulate the activity of the subject's immune system and enhance the immune response. The administration of the vaccine can be the transfection of the cancer antigens as disclosed herein as a nucleic acid molecule that is expressed in the cell and delivered to the surface of the cell, whereupon the immune system recognizes and induces a cellular, humoral, or cellular and humoral response. The administration of the vaccine can be used to induce or elicit an immune response in subjects against one or more of the cancer antigens as disclosed herein by administering to the subject the vaccine as discussed herein.

The vaccine can be administered to a subject to modulate the activity of the subject's immune system, thereby enhancing the immune response. In some embodiments, the subject is a mammal. Upon administration of the vaccine to the mammal, and thereby introducing the vector into the cells of the mammal, the transfected cells will express and secrete one or more of the cancer antigens as disclosed herein. These secreted proteins, or synthetic antigens, will be recognized as foreign by the immune system, which will mount an immune response that can include: antibodies made against the one or more cancer antigens, and T-cell response specifically against the one or more cancer antigens. In some examples, a mammal vaccinated with the vaccines discussed herein will have a primed immune system and when challenged with the one or more cancer antigens as disclosed herein, the primed immune system will allow for rapid clearing of subsequent cancer antigens as disclosed herein, whether through the humoral, cellular, or both cellular and humoral immune responses.

Methods of administering the DNA of a vaccine are described in U.S. Pat. Nos. 4,945,050 and 5,036,006, both of which are incorporated herein in their entirety by reference.

The vaccine can be administered to a mammal to elicit an immune response in a mammal. The mammal can be human, non-human primate, cow, pig, sheep, goat, antelope, bison, water buffalo, bovids, deer, hedgehogs, elephants, llama, alpaca, mice, rats, and preferably human, cow, or pig. The vaccine can likewise be administered to a non-mammal subject, for example, a chicken, to elicit an immune response.

The vaccine dose can be between 1 microgram and 10 mg active component per kilogram (kg) body weight over time (component/kg body weight/time), and can be 20 micrograms to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, 10, or more doses.

Methods of Generating an Immune Response with the Vaccine

The vaccine can be used to generate an immune response in a mammal or non-mammal subject, including therapeutic or prophylactic immune response. The immune response can generate antibodies and/or killer T cells directed to the one or more cancer antigens as disclosed herein. Such antibodies and T cells can be isolated.

Some embodiments provide methods of generating immune responses against one or more of the cancer antigens as disclosed herein, which embodiments comprise administering the vaccine to a subject. Some embodiments provide methods of prophylactically vaccinating a subject against a cancer or tumor expressing one or more of the cancer antigens as described above, which embodiments comprise administering the vaccine. Some embodiments provide methods of therapeutically vaccinating a subject that has been suffering from the cancer or tumor expressing one or more of the cancer antigens, which embodiments comprise administering the vaccine. Diagnosis of the cancer or tumor expressing the one or more cancer antigens as disclosed herein prior to administration of the vaccine can be done routinely.

Methods of Cancer Treatment with the Vaccine

The vaccine can be used to generate or elicit an immune response in a mammal that is reactive or directed to a BORIS-expressing cancer or tumor (e.g., ovarian cancer) of the mammal or subject in need thereof. The elicited immune response can prevent cancer or tumor growth.

The elicited immune response can prevent and/or reduce metastasis of cancerous or tumor cells. Accordingly, the vaccine can be used in a method that treats and/or prevents cancer or tumors in the mammal or subject administered the vaccine.

Routes of Administration

The vaccine or pharmaceutical composition can be administered by different routes including orally, parenterally, sublingually, transdermally, rectally, transmucosally, topically, via inhalation, via buccal administration, intrapleurally, intravenously, intraarterially, intraperitoneally, subcutaneously, intramuscularly, intranasal intrathecally, and/or intraarticularly, or combinations thereof. For veterinary use, the composition can be administered as a suitably acceptable formulation in accordance with normal veterinary practice. The veterinarian can readily determine the dosing regimen and route of administration that is most appropriate for a particular animal. The vaccine can be administered by traditional syringes, needleless injection devices, "microprojectile bombardment gene guns", or other physical methods such as electroporation ("EP"), "hydrodynamic method", or ultrasound.

The vector of the vaccine can be administered to the mammal by several well-known technologies including DNA injection (also referred to as DNA vaccination) with and without in vivo electroporation, liposome mediated transfection, nanoparticle facilitated transfection, and use recombinant vectors such as recombinant adenovirus, recombinant adenovirus associated virus, and recombinant vaccinia. The one or more cancer antigens of the vaccine can be administered via DNA injection along with in vivo electroporation.

The vaccine or pharmaceutical composition comprising the vaccine can be administered by electroporation. Administration of the vaccine via electroporation can be accomplished using electroporation devices that can be configured to deliver to a desired tissue of a mammal a pulse of energy effective to cause reversible pores to form in cell membranes, and preferably the pulse of energy is a constant current similar to a preset current input by a user. The electroporation device can comprise an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation can be accomplished using an in vivo electroporation device, for example CELLECTRA® EP system (Inovio Pharmaceuticals, Inc., Blue Bell, Pa.) or Elgen electroporator (Inovio Pharmaceuticals, Inc.) to facilitate transfection of cells by the plasmid.

Examples of electroporation devices and electroporation methods that can facilitate administration of the DNA vaccines of the present invention include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that can be used for facilitating administration of the DNA vaccines include those provided in co-pending and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems can comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then administering via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference in its entirety.

U.S. Patent Pub. 2005/0052630 submitted by Smith, et al. describes an electroporation device that can be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby fully incorporated by reference.

The electrode arrays and methods described in U.S. Pat. No. 7,245,963 and U.S. Patent Pub. 2005/0052630 can be adapted for deep penetration into not only tissues such as muscle, but also other tissues or organs. Because of the configuration of the electrode array, the injection needle is also inserted completely into the target organ, and the injection is administered perpendicular to the target issue, in the area that is pre-delineated by the electrodes. The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns administration of DNA using any of a variety of devices, and U.S. Pat. No. 7,328,064 issued Feb. 5, 2008, drawn to method of injecting DNA are contemplated herein. The above-patents are incorporated by reference in their entirety.

Methods of Preparing the Vaccine

Provided herein are methods for preparing the vectors that comprise the nucleic acid molecule(s) encoding synthetic consensus BORIS antigen discussed herein. The DNA vectors, after the final subcloning step into the mammalian expression plasmid, can be used to inoculate a cell culture in a large-scale fermentation tank, using known methods in the art.

The DNA vectors for use with the EP devices of the present invention can be formulated or manufactured using a combination of known devices and techniques, but preferably they are manufactured using an optimized plasmid manufacturing technique that is described in US published application no. 20090004716, which was filed on May 23, 2007. In some examples, the DNA vectors used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

The present invention has multiple aspects, illustrated by the following non-limiting examples.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1—Generation of Synthetic Consensus BORIS Antigen

In order to generate a human consensus BORIS, 7 BORIS sequences were collected from GenBank (https://www.ncbi.nlm.nih.gov/genbank/). The GenBank accession numbers for selected BORIS subfamily 1 sequences are: NP 542185.2, XP_009435727.1, XP_004062465.1, XP_002830505.1, XP_003806212.1, XP_011833550.1, and XP_0032530231

A consensus sequence was generated using the DNAS-TAR® Lasergene software package (version 13.0.0.357). The seven sequences listed above were imported into MegAlign and aligned using the ClustalW multiple sequence alignment program. The resulting BORIS consensus sequence shares 98.6% identity with human native BORIS.

In order to abolish the potential biological function of the consensus BORIS sequence, 22 mutations (2 mutations in each of the 11 zinc fingers) were introduced to disrupt zinc finger structure and DNA binding potential. In addition, since BORIS is a transcription factor, one mutation was introduced to prevent nuclear localization. The rationale for the introduction of these mutations is described below.

Zinc Finger Mutations

CTCF and CTCFL (BORIS) are paralogous genes that have the same exons encoding the 11-zinc finger domain (and the same DNA-binding potential). The cysteines in the eleven zinc fingers in consensus BORIS were mutated to glycines to disrupt zinc finger structure and binding.

Nuclear Localization Signal (NLS) Mutations

As BORIS is a transcription factor, a predicted nuclear localization signal was identified using the Stockholm Bioinformatics Center NucPred program (www.sbc.su.se/~macallr/nucpred/cgi-bin/single.cgi). The predicted nuclear localization signal in BORIS has the type of class 1 monopartite NLS with four consecutive basic amino acids. To prevent nuclear localization, the nuclear localization signal was mutated from RKRK to RRRK.

After generation of the consensus BORIS sequence and subsequent mutations in the zinc finger and NLS DNA sequences, the resulting synthetic consensus BORIS antigen protein sequence shares 95.2% identity with human native BORIS protein isoform "sf1" (i.e., NP_542185.2).

Once the synthetic consensus BORIS antigen DNA sequence was obtained, in order to have a higher level of expression, an upstream Kozak sequence and IgE leader sequence were added to the N-terminus. Furthermore, the codon usage of this gene was adapted to the codon bias of *Homo sapiens* genes. (Andre, S. et al. Increased immune response elicited by DNA vaccination with a synthetic gp120 sequence with optimized codon usage. Journal of virology 72, 1497-1503 (1998); Deml, L. et al. Multiple effects of codon usage optimization on expression and immunogenicity of DNA candidate vaccines encoding the human immunodeficiency virus type 1 Gag protein. *Journal of virology* 75, 10991-11001, doi:10.1128/JVI.75.22.10991-11001.2001 (2001)). In addition, RNA optimization was also performed: regions of very high (>80%) or very low (<30%) GC content and the cis-acting sequence motifs such as internal TATA boxes, chi-sites and ribosomal entry sites were avoided. (Muthumani, K. et al. Novel engineered HIV-1 East African Clade-A gp160 plasmid construct induces strong humoral and cell-mediated immune responses in vivo. Virology 314, 134-146 (2003); Schneider, R., Campbell, M., Nasioulas, G., Felber, B. K. & Pavlakis, G. N. Inactivation of the human immunodeficiency virus type 1 inhibitory elements allows Rev-independent expression of Gag and Gag/protease and particle formation. Journal of virology 71, 4892-4903 (1997)). The synthetic consensus BORIS antigen DNA sequence was digested with BamHI and XhoI, and cloned into a proprietary expression vector pGX0001 with the expression cassette placed under the transcription control of the cytomegalovirus immediate-early promoter. The resulting plasmid was designated pGX1440 and full-length sequencing was performed and then analyzed and confirmed to be correct. A schematic representation of the synthetic consensus BORIS antigen DNA construct is shown in FIG. 1. The nucleotide and amino acid sequences of the synthetic consensus BORIS antigen of the invention are set forth in SEQ ID NO:1 and SEQ ID NO:2, respectively. The characteristics of synthetic consensus BORIS antigen DNA and protein sequences are summarized in Table 2 below.

TABLE 1

| Features of SEQ ID NO: 2 | |
|---|---|
| Feature | Amino acid position |
| IgE leader sequence | 1-18 |
| BORIS coding sequence | 19-680 |
| Mutations to disrupt zinc finger binding | C276G, C279G, C304G, C307G C332G, C335G, C361G, C364G C389G, C392G, C417G, C420G C447G, C450G, C477G, C480G C505G, C508G, C533G, C536G C565G, C568G |
| Mutation to disrupt GPI-attachment | K603R |

TABLE 2

| Characteristics of synthetic consensus BORIS antigen | |
|---|---|
| Characteristics | synthetic consensus BORIS antigen (SEQ ID NO: 2) |
| Identity to native human BORIS | 95.2% |
| Identity to native rhesus BORIS | 81.5 to 91.8% |
| Identity to native mouse BORIS | 56.5 to 57.4% |
| Number of amino acid mutations (vs native human) | 32 |
| Number of inserted mutations (not consensus derived) | 23 |

TABLE 2-continued

Characteristics of synthetic consensus BORIS antigen

| Characteristics | synthetic consensus BORIS antigen (SEQ ID NO: 2) |
|---|---|
| Molecular weight | 680 aa (75 KDa) |
| Length of coding sequence (bp) | 2046 |

Example 2—Construction of pGX1440 BORIS Expression Vectors pGX0001 (a modified pVAX1 expression vector) under the control of the human cytomegalovirus immediate-early promoter (hCMV promoter), was used as a backbone vector. The original pVAX1 was obtained from Thermo Fisher Scientific.

Modifications were introduced into pVAX1 to create pGX0001 and are identified based on the reported sequence of pVAX1 available from Thermo Fisher Scientific. These modifications are listed below and no issues have been detected regarding plasmid amplification and antigen transcription and translation. No further changes in the sequence of pGX0001 have been observed to date in any of the plasmid products in the platform using pGX0001 as the backbone.

| Modification | Base Pair | Description |
|---|---|---|
| C > G | 241 | in CMV promoter |
| C > T | 1158 | backbone, downstream of the bovine growth hormone polyadenylation signal (bGH polyA) |
| A > - | 2092 | backbone, downstream of the Kanamycin resistance gene |
| C > T | 2493 | in pUC origin of replication (pUC ori) |
| G > C | 2969 | in very end of pUC On upstream of RNASeH site |

Figure 4:
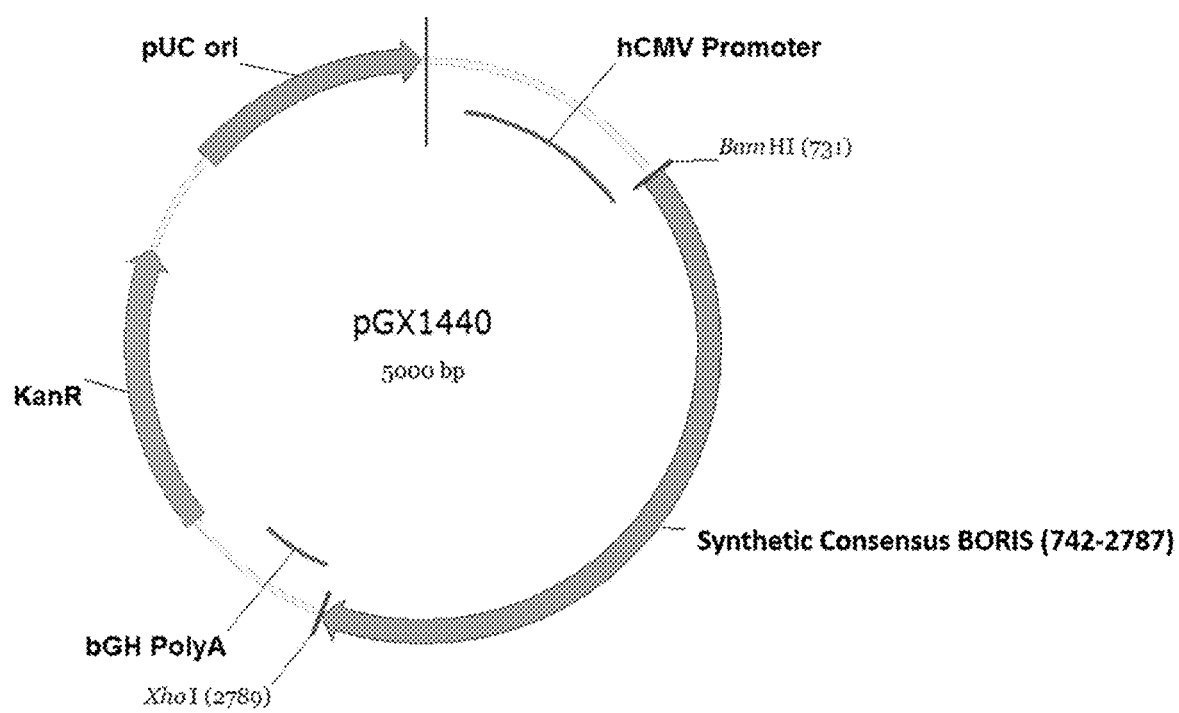
FIG. 4 shows the construction of pGX1440 including the synthetic consensus BORIS antigen sequence insert.

Base pairs 2, 3 and 4 are changed from ACT to CTG in backbone, upstream of CMV promoter.

pGX1440 is a DNA plasmid encoding the synthetic consensus BORIS antigen protein. Related mRNA production is driven by a human CMV promoter (hCMV promoter) and terminated by the bovine growth hormone 3' end polyadenylation signal (bGH polyA). The pGX0001 backbone includes the kanamycin resistance gene (KanR) and plasmid origin of replication (pUC ori) for production purpose. Those elements are not functional in eukaryotic cells. pGX1440 was made by cloning the synthetic consensus BORIS antigen DNA sequence into pGX0001 at the BamHI and XhoI sites, as illustrated in FIG. 4.

Example 3—Immunogenicity of Synthetic Consensus BORIS Antigen Constructs

Immunogenicity of the vaccine construct designed to target human BORIS, synthetic consensus BORIS antigen (pGX1440), was evaluated in mice. Expression of the antigen protein by the construct was also evaluated in vitro by Western blotting.

Materials and Methods
Plasmids

For in vitro and in vivo studies, plasmid (10 mg) was ordered from GenScript for pGX1440 (lot # U0638BC040S-3/G61425). Antigen sequence of the 10 mg plasmid stock was confirmed by Sanger sequencing and confirmed for accuracy.

In Vitro Antigen Expression

Expression of the antigen protein by pGX1440 was confirmed by western blotting. Human rhabdomyosarcoma (RD) cells (ATCC, CCL-136) maintained in DMEM medium with 10% FBS (ThermoFisher) were transfected with pGX1440 or pGX0001 (6 µg/10 cm$^2$ dish) using Turbofectin 8 (Origene). Forty-eight hours after transfection, the cells were lysed using RIPA cell lysis buffer (ThermoFisher) and cell lysate was collected. Following a BCA assay (ThermoFisher) to determine total protein concentration, 15 µg of cell lysate was electrophoresed on a 4-12% SDS-PAGE gel (ThermoFisher) and detection was performed with an anti-BORIS (CTCFL) monoclonal antibody (AbCam, clone 126778) then visualized with horseradish peroxidase (HRP)-conjugated anti-mouse IgG (Santa Cruz Biotech, sc-2005) using an ECL western blot analysis system (GE Amersham). As a loading control, blots were re-probed for actin expression using an anti-β-actin monoclonal antibody (Santa Cruz Biotech, clone, C4).

Animals and Immunizations

Female, 8-week-old CB6F1 mice were purchased from Jackson Laboratories. All animals were housed in a temperature-controlled, light-cycled facility at BTS Research (San Diego, Calif.). Animal care was carried out according to the guidelines of the National Institutes of Health and the Animal Care and Use Proposal (ACUP) (BTS ACUP #15-091). Mice were divided into five groups as detailed in Table 3.

TABLE 3

Study Groups

| Group | n | Construct | Construct Dose (µg) | Injection volume (µL) |
|---|---|---|---|---|
| 1 | 4 | pGX0001 | 30 | 30 |
| 2 | 8 | pGX1440 | 10 | 30 |
| 3 | 8 | pGX1440 | 20 | 30 |
| 4 | 8 | pGX1440 | 30 | 30 |
| 5 | 8 | pGX1440 | 50 | 30 |

The mice in the immunized groups were vaccinated with the doses indicated of pGX0001 or pGX1440. Briefly, plasmids were formulated in sterile water for injection (VetOne) such that the indicated dose was delivered by intramuscular injection into the tibialis anterior muscle in a 30 µL injection volume. Each intramuscular injection was immediately followed by electroporation (EP) using the CELLECTRA® 2000 Adaptive Constant Current Electroporation Device with a 3P array (Inovio Pharmaceuticals). The device was configured to deliver two 0.1 Amp pulses of 52 ms pulse width, spaced apart by a 1 second delay. The mice received 3 immunizations, 3 weeks apart. Mice were sacrificed one week after the last immunization and spleens harvested for cellular immune readouts. No other tissue was collected.

Splenic Lymphocyte Isolation

Splenocytes were aseptically isolated and placed in 5 mL of R10 media (Rosewell Park Memorial Institute medium 1640 supplemented with 10% fetal bovine serum and 1% antibiotic-antimycotic). Splenocytes were isolated by mechanical disruption of the spleen using a Stomacher machine (Seward Laboratory Systems Inc.), and the resulting product was filtered using a 40-µm cell strainer (BD Falcon). The resulting product was centrifuged and the pellet was treated for 5 min with ACK lysis buffer (Lonza) for lysis of red blood cells. The splenocytes were then centrifuged, washed in PBS, and then resuspended in R10 media and immediately used for further analysis.

IFNγ ELISpot

Figure 7A:
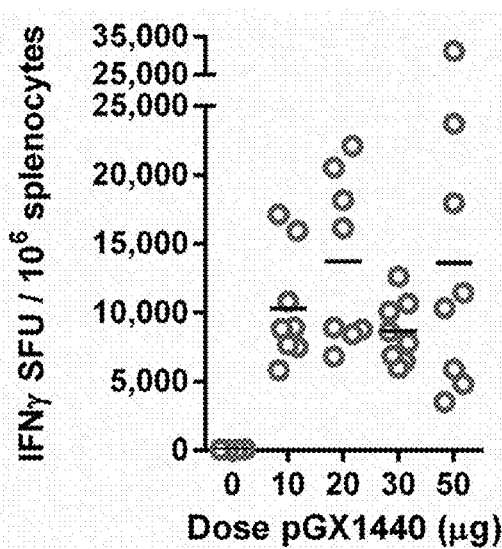
FIGS. 7A and 7B show immunogenicity of synthetic consensus BORIS antigen. Female CB6F1 mice were immunized 3 times, 3 weeks apart with the indicated doses of synthetic consensus BORIS antigen (pGX1440, n=8/group), or pGX0001 (empty vector, n=4). Synthetic consensus BORIS antigen-specific IFNγ responses were assessed by ELISpot at indicated doses of pGX1440.
Figure 7B:
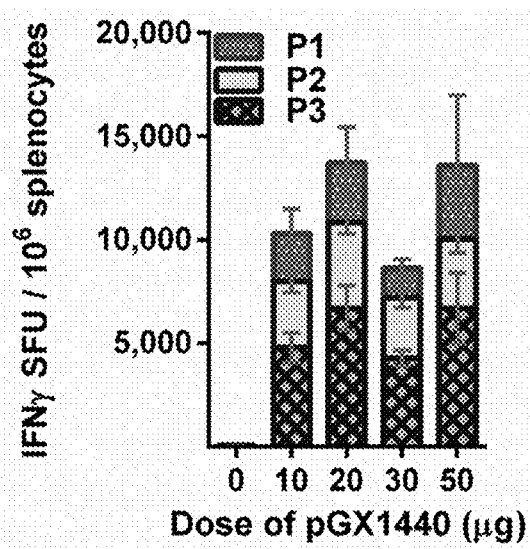

Mouse IFNγ ELISpot assay (MabTech) was performed to evaluate antigen-specific cellular responses. Briefly, 96 well plates pre-coated with anti-mouse IFNγ antibody were washed in PBS and blocked for 2 hours at room temperature with complete culture medium (RPMI 1640 supplemented with 10% FBS and antibiotics). Splenic lymphocytes were re-suspended in R10 media (and then added in triplicates at an input cell number of $2 \times 10^5$ cells per well. A set of peptides was synthesized (GenScript), each containing 15 amino acid residues overlapping by 11 amino acids representing the entire synthetic consensus BORIS antigen protein sequence. These sets of peptides were resuspended in DMSO (Sigma) and pooled at a concentration of ~2 μg/ml peptide into three peptide pools (P1, P2, and P3 in FIG. 7B). The peptide pool contained the peptides corresponding to the synthetic consensus BORIS antigen. Concavalin A (Sigma) at 5 μg/ml was used as a positive control and complete culture medium was used as a negative control. Plates were incubated for 18 hours at 37° C., in a 5% $CO_2$ atmosphere incubator. Then, a biotinylated anti-mouse IFNγ detection antibody (MabTech) was added, and plates were incubated for 2 hours at room temperature. The plates were washed, and Streptavidin-ALP antibody (MabTech) was added and plates incubated for 1 hour at room temperature. Spot detection was completed according to the kit manufacturer's instructions (MabTech). The spots on the plates were counted using an automated ELISPOT reader (Cellular Technology). The average number of Spot Forming Units (SFU) was adjusted to $1 \times 10^6$ splenocytes for data display.

Antigen specific responses by IFNγ ELISpot are reported as the number of IFNγ spot forming unit (SFU) per $1 \times 10^6$ splenocytes greater than the SFU in the media only control.

Flow Cytometry

Figure 5:
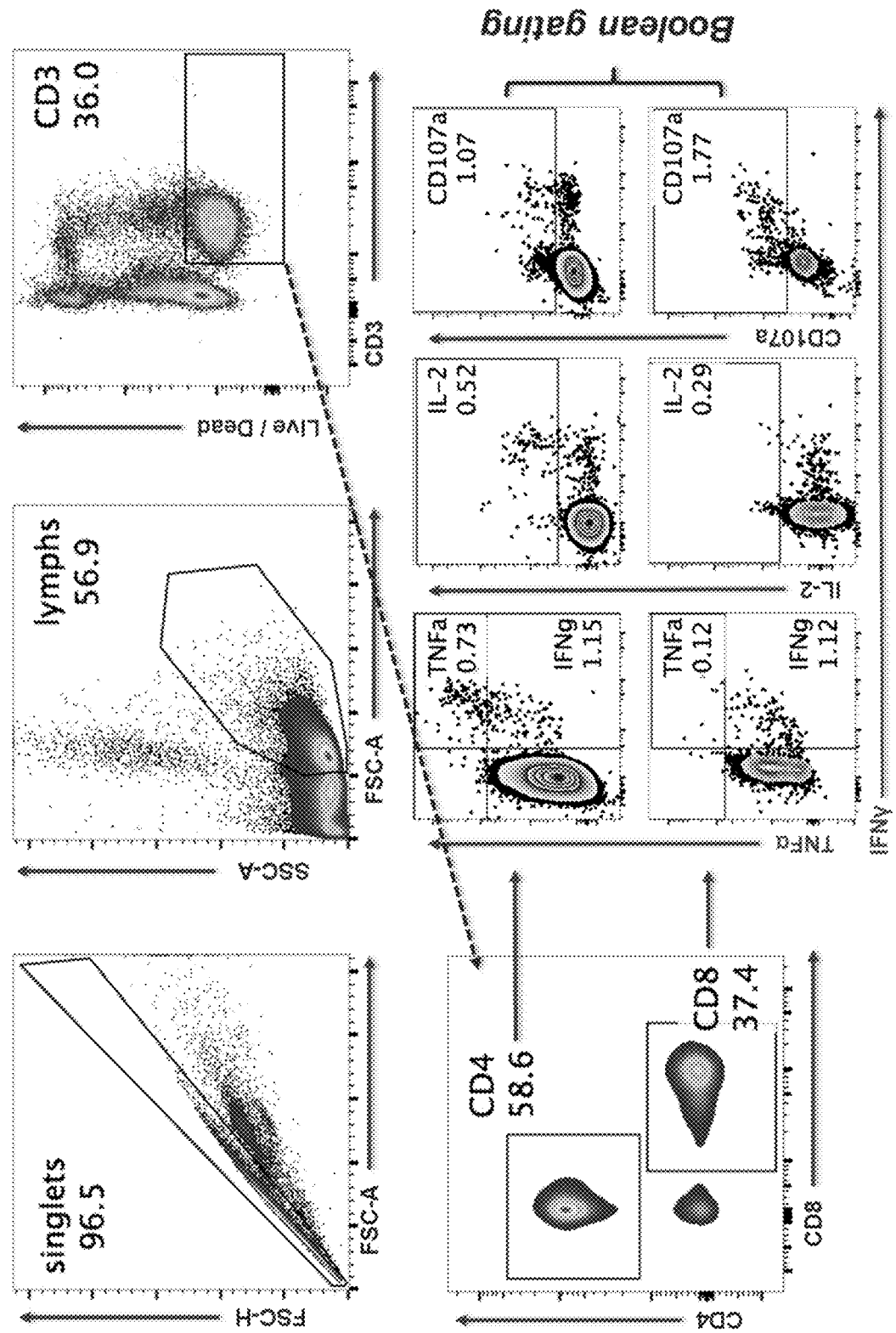
FIG. 5 shows the flow cytometry gating strategy.

Cellular immune responses induced by synthetic consensus BORIS antigen were further characterized by flow cytometry. Briefly, $2 \times 10^6$ splenocytes from vaccinated and naïve mice were immediately stimulated following isolation with the synthetic consensus BORIS antigen peptides for 6 hours in the presence of Brefeldin A (BD Biosciences), Monensin (BD Biosciences), and FITC anti-mouse CD107a antibody (BD Biosciences). After stimulation with peptides, splenocytes were spun down and resuspended in 20 μL per well of mouse BD Fc Block (BD Biosciences) solution. The Fc Block is used at an initial dilution of 1:40 in PBS and incubated at 4° C. for 5 minutes. After incubation, the remaining extracellular antibodies (in PBS) are added at 30 μL per well and allowed to incubate at 4° C. for 30 minutes. Upon addition of the extracellular stain, the final volume in each well is 50 μL, consisting of Fc Block at a final dilution of 1:100 and the extracellular antibodies at their appropriate working dilutions. Cells were then stained with viability dye (Vivid, Thermo-Fisher) and the following extracellular antibodies: APC-Cy7 anti-mouse CD3e, PerCP-Cy5.5 anti-mouse CD4, and APC anti-mouse CD8a (BD Biosciences). Intracellular cytokines were subsequently stained with the following antibodies: BV605 anti-mouse IFNγ, APC-R700 anti-mouse IL-2, and PE anti-mouse TNF-α (BD Biosciences). ICS data was collected on 10-color FACS CANTO (BD Biosciences) and analysis completed using FlowJo. The flow cytometry gating strategy is shown in FIG. 5.

For a cell to be called antigen specific by flow cytometry, the frequency of the reported parameter must exceed that of the media-only control. For a cell to be identified as producing antigen specific CD107a, the cell must also be identified as positive for antigen specific production of IFNγ, and/or IL-2 and/or TNFα as identified by Boolean gating.

Statistical Analysis

Statistical analysis was completed using IBM SPSS Statistics 22 (IBM Corporation). Analysis between groups was performed using an ANOVA with post-hoc Tukey's Honest Significant Difference (HSD) to adjust for multiple comparisons. Homogeneity of variance was confirmed using the F statistic prior to multiple comparisons. For all statistical analysis, a p-value of 0.050 was considered significant.

Results

Expression of the Synthetic Consensus BORIS Antigen

Figure 6:
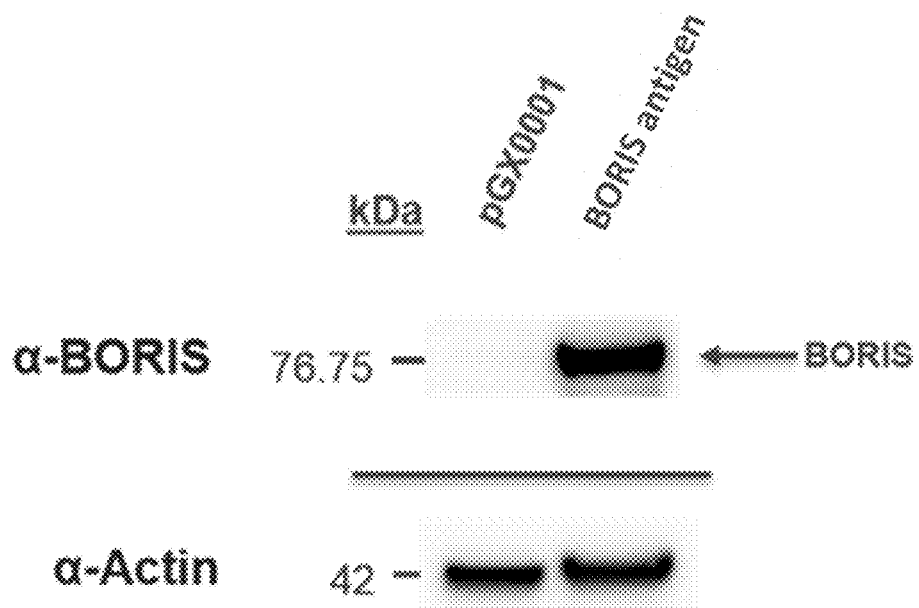
FIG. 6 shows in vitro expression of the synthetic consensus BORIS antigen in human rhabdomyosarcoma (RD) cells transfected with pGX1440 as determined by immunoblotting with an anti-human BORIS antibody.

Expression of the synthetic consensus BORIS antigen by pGX1440 was confirmed by western blotting. Briefly, human rhabdomyosarcoma (RD) cells were transfected with the pGX1440 or pGX0001 (empty vector, negative control) plasmids. Cell lysates were probed for expression of the synthetic consensus BORIS antigen with an anti-human BORIS antibody (CTCFL). A protein band of the expected molecular weight for synthetic consensus BORIS antigen (76.75 kD) was detected (FIG. 6). A faint band was detected in the negative control (pGX0001) that is most likely due to low level endogenous BORIS protein expression in the RD cell line. Anti-β-actin bands were detected of similar intensities indicating equal amounts of protein were loaded in each lane. In summary, pGX1440 was found to express its respective antigen protein.

Immunogenicity of the Synthetic Consensus BORIS Antigen Vaccine Constructs

IFNγ ELISpot

Immunogenicity of the synthetic consensus BORIS antigen construct was evaluated at four doses (10 μg, 20 μg, 30 μg, and 50 μg) by IFNγ ELISpot and flow cytometry (n=8/group). Mice were immunized with the empty plasmid backbone (pGX0001) as a negative control (n=4/group). Vaccination with synthetic consensus BORIS antigen (pGX1440) induced exceptionally robust cellular immune responses compared to negative control vaccinated mice. The magnitude of synthetic consensus BORIS antigen specific IFNγ production, as determined by ELISpot, was dose-independent (FIG. 7) with a similar maximal response achieved at both the 20 and 50 μg dose. Specifically, synthetic consensus BORIS antigen specific IFNγ SFU were 10,315±4,093, 13,725±6,151, 8,645±2,304, and 13,600±9,894 at the 10 μg, 20 μg, 30 μg, and 50 μg respectively. Synthetic consensus BORIS antigen IFNγ responses were significantly greater than naïve at the 10 μg (p=0.026), 20 μg (p=0.002), and 50 μg (p=0.003) doses of pGX1440, but not at the 30 μg dose (p=0.071). IFNγ responses are summurized in Table 4.

TABLE 4

IFNγ responses induced by synthetic consensus BORIS antigen
Synthetic Consensus BORIS antigen (pGX1440)

| Construct | Dose | Mean SFU ± Std. Dev. | p-value |
|---|---|---|---|
| pGX0001 | 30 μg | 50 ± 24 | n/a |
| pGX1440 | 10 μg | 10,315 ± 4,093 | 0.026 |
|  | 20 μg | 13,725 ± 6,151 | 0.002 |
|  | 30 μg | 8,645 ± 2,304 | 0.071 |
|  | 50 μg | 13,600 ± 9,894 | 0.003 |

Statistical significance assumed at p ≤ 0.05 p-values reported are relative to naive (pGX0001 immunized mice).

Flow Cytometry

Figure 8B:
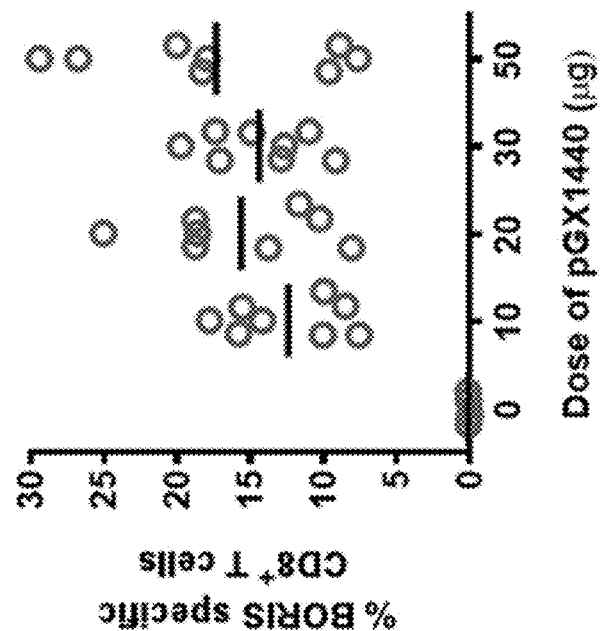
FIGS. 8A, 8B, 8C, and 8D show relative frequency of CD4+ and CD8+ T cells. Cellular immune responses induced by pGX1440 were predominantly in the CD8+ T cell compartment relative to the CD4+ T cell compartment. Synthetic consensus BORIS antigen induced frequencies of antigen specific $CD4^+$ T cell responses that were significantly more robust than naïve in all dose groups (FIG. 8A). The frequency of antigen specific $CD8^+$ T cells induced by synthetic consensus BORIS antigen significantly increased over control in all dose groups (FIG. 8B). Cytokine profile of synthetic consensus BORIS antigen-specific CD4+ T cell (FIG. 8C) and CD8+ T cell responses is shown in (FIG. 8D).
Figure 8A:
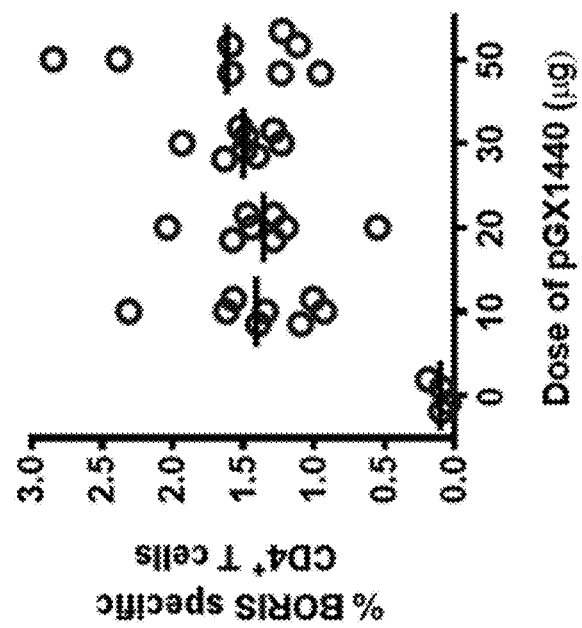
Figure 8C:
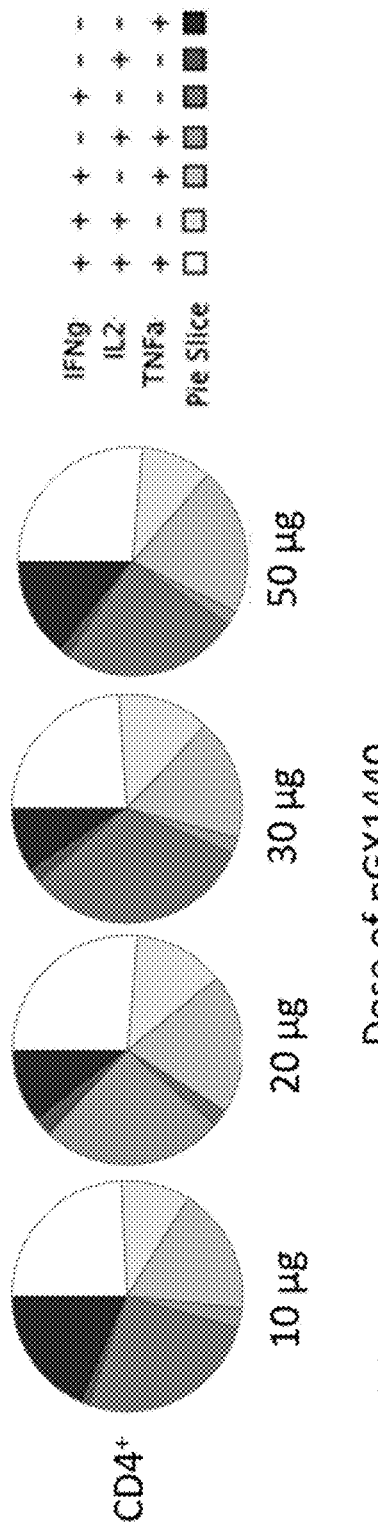

Synthetic consensus BORIS antigen elicited more robust responses in the CD8+ T cell compartment, relative to the responses in the CD4+ T cell compartment (FIGS. 8A, 8B, 8C, and 8D). Synthetic consensus BORIS antigen induced frequencies of antigen specific CD4+ T cell responses that were significantly more robust than naïve (0.11%±0.06%) in the 10 µg (1.41%±0.44%) (p<0.001), 20 µg (1.36%±0.42%) (p<0.001), 30 µg (1.50%±0.22%) (p<0.001) and 50 µg (1.62%±0.66%) (p<0.001) dose groups (FIG. 8A). Synthetic consensus BORIS antigen specific CD4+ T cell responses were also dose independent and consisted mainly of IFNγ+IL-2+TNFα+, IFNγ+IL-2−TNFα+ or IFNγ+IL-2−TNFα− producing CD4+ T cells (FIG. 8C). The frequency of antigen specific CD4+ T cells is further detailed in Table 5.

TABLE 5

CD4+ T cell responses induced by synthetic consensus BORIS antigen
Synthetic Consensus BORIS antigen CD4+ T cells

| Construct | Dose | % CD4+ ± Std. Dev. | p-value |
|---|---|---|---|
| pGX0001 | 30 µg | 0.11 ± 0.06 | n/a |
| pGX1440 | 10 µg | 1.41 ± 0.44 | <0.001 |
|  | 20 µg | 1.36 ± 0.42 | <0.001 |
|  | 30 µg | 1.50 ± 0.22 | <0.001 |
|  | 50 µg | 1.62 ± 0.66 | <0.001 |

Statistical significance assumed at p ≤ 0.05.
p-values reported are relative to naïve (pGX0001 immunized mice)

Figure 8D:
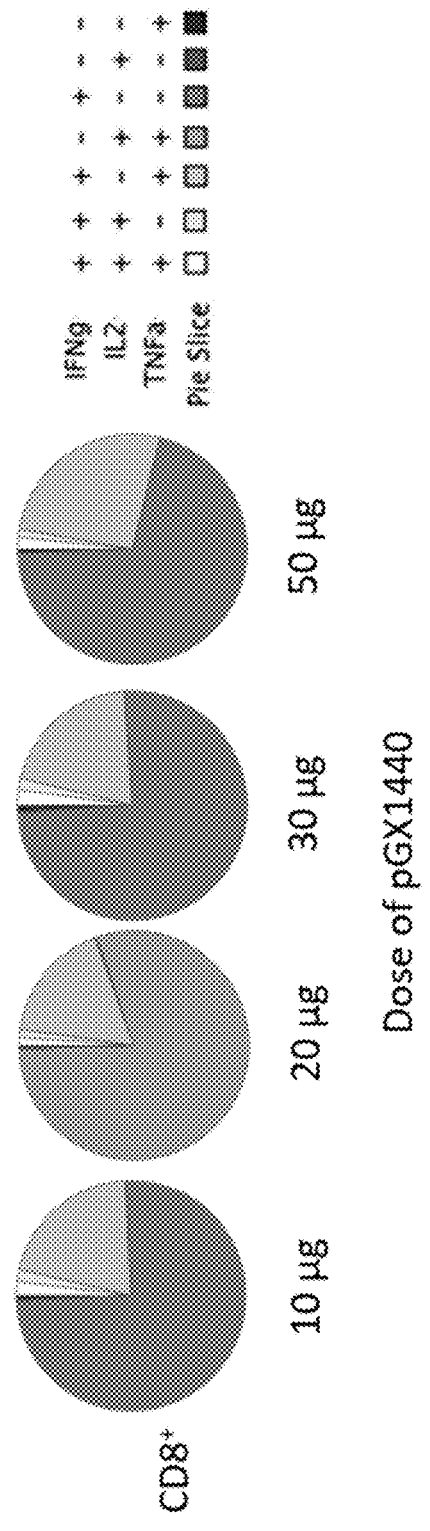

The frequency of antigen specific CD8+ T cells induced by synthetic consensus BORIS antigen significantly increased over control in all dose groups (FIG. 8B). Specifically, the frequency of antigen specific CD8+ T responses in the groups immunized with 10 µg (12.45%±3.86%) (p=0.002), 20 µg (15.64%±5.63%) (p<0.001), 30 µg (14.49%±3.58%) (p<0.001), and 50 µg (17.34%±8.17%) of pGX1440 was significantly more robust compared to naïve (0.10%±0.05%). Synthetic consensus BORIS antigen specific CD8+ T cell responses were also dose independent and consisted mainly of IFNγ+IL-2−TNFα− and IFNγ+IL-2−TNFα+ producing CD8+ T cells (FIG. 8D). The frequency of antigen specific CD8+ T cells is further detailed in Table 6.

TABLE 6

CD8+ T cell responses induced by synthetic consensus BORIS antigen
Synthetic consensus BORIS antigen CD8+ T cells

| Construct | Dose | % CD8+ ± Std. Dev. | p-value |
|---|---|---|---|
| pGX0001 | 30 µg | 0.10 ± 0.05 | n/a |
| pGX1440 | 10 µg | 12.45 ± 3.86 | 0.002 |
|  | 20 µg | 15.64 ± 5.63 | <0.001 |
|  | 30 µg | 14.49 ± 3.58 | <0.001 |
|  | 50 µg | 17.34 ± 8.17 | <0.001 |

Statistical significance assumed at p ≤ 0.05.
p-values reported are relative to naïve (pGX0001 immunized mice)

Figure 9A:
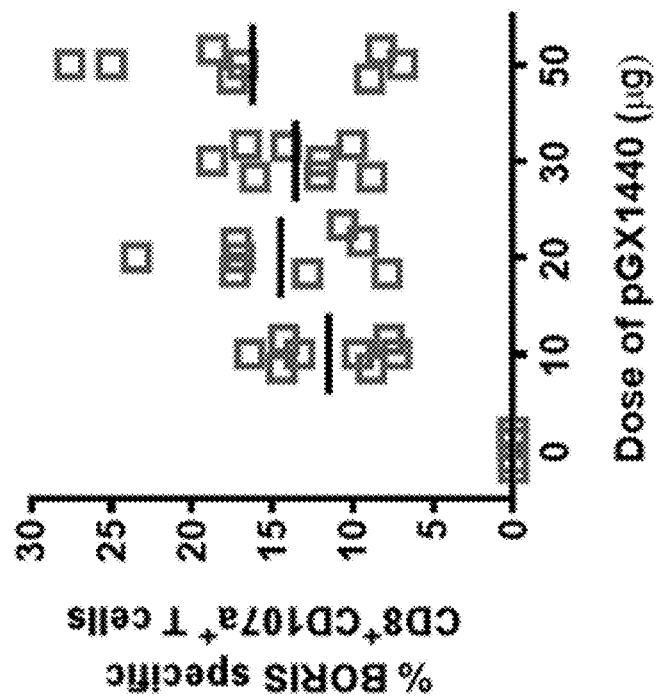
FIGS. 9A, 9B, 9C, and 9D show cytolytic potential of synthetic consensus BORIS antigen-specific T cells. Cytolytic immune responses induced by pGX1440 were predominantly in the CD8+ T cell compartment relative to the CD4+ T cell compartment. The frequency of antigen specific $CD4^+CD107a^+$ T cells was increased in all dose groups (FIG. 9A). Similarly, the frequency of antigen specific $CD8^+CD107a^+$ T cells was increased in all dose groups, (FIG. 9B). Cytokine profile of CD4+CD107a+ T cells (FIG. 9C) and CD8+CD107a+ T cells is shown in (FIG. 9D).
Figure 9B:
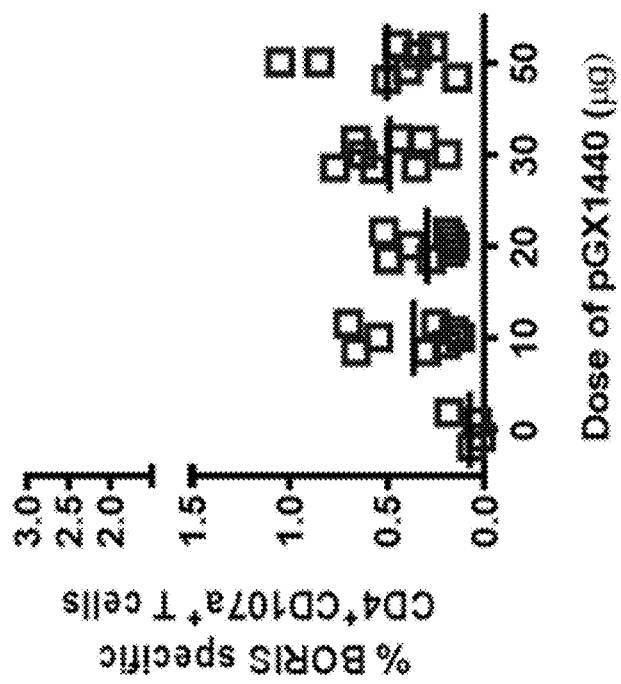
Figures 9C, 9D:
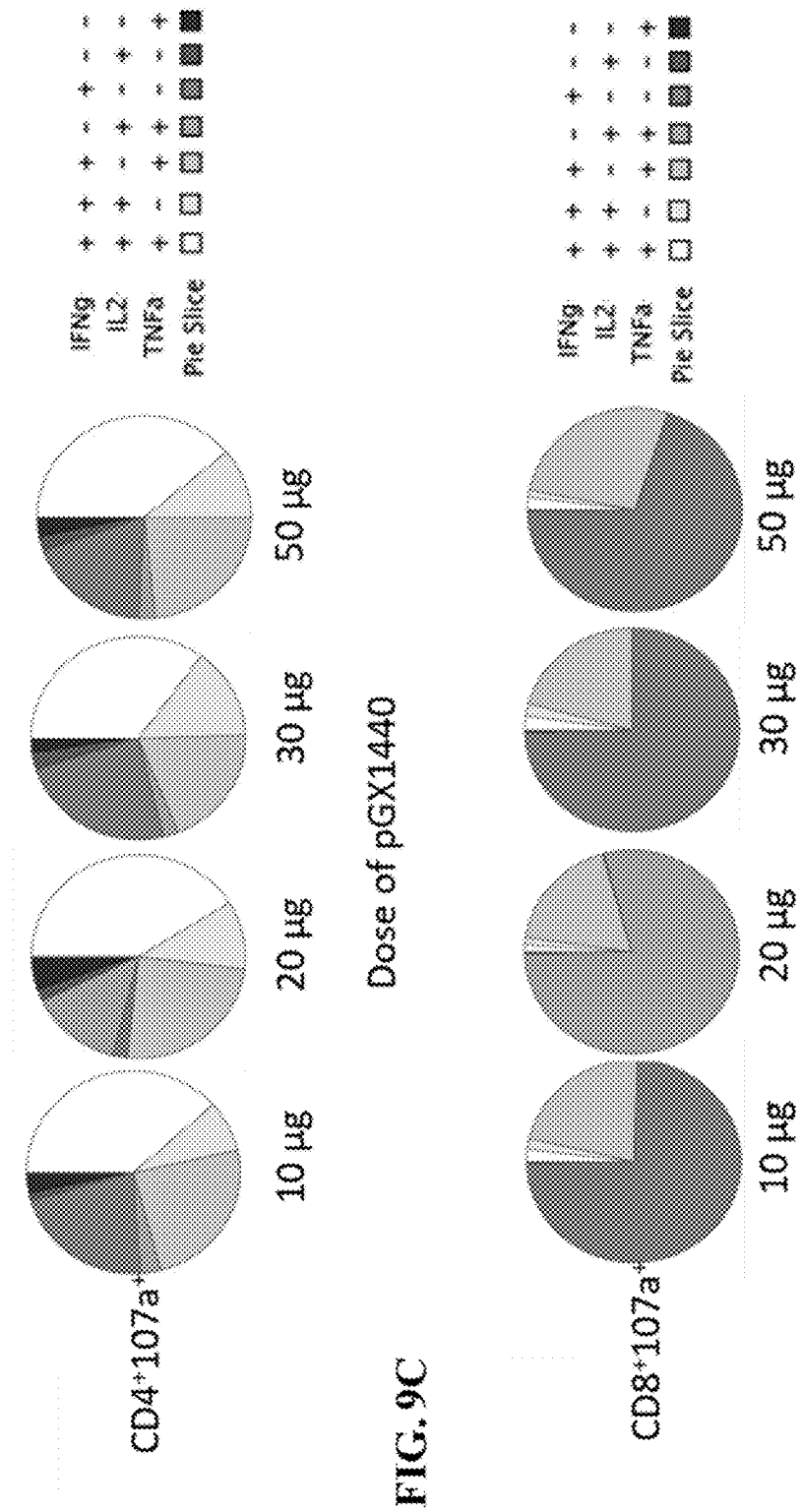

All doses of synthetic consensus BORIS antigen induced a frequency of CD4+CD107a+ T cells that was greater than naïve (0.08%±0.07%) but only the higher doses of 30 µg and 50 µg were significantly more robust. Specifically, the frequency of antigen specific CD4+CD107a+ T cells was 0.37%±0.23%, 0.30%±0.15%, 0.49%±0.20%, and 0.50%±0.30% in the 10 µg (p=0.097), 20 µg (p=0.256), 30 µg (p=0.012), and 50 µg (p=0.010) dose groups, respectively (FIG. 9A). The cytokine profile of synthetic consensus BORIS antigen specific CD4+CD107a+ T cells was similar across dose groups and was comprised mainly of IFNγ+IL-2+TNFα+, IFNγ+IL-2−TNFα+, IFNγ+IL-2−TNFα− cells (FIG. 9C). The frequency of antigen specific CD4+ T cells with cytolytic potential is further detailed in Table 7.

TABLE 7

Cytolytic potential of antigen specific CD4+ T cells induced by synthetic consensus BORIS antigen
Synthetic consensus BORIS antigen CD4+CD107a+ T cells

| Construct | Dose | % CD4+CD107a+ ± Std. Dev. | p-value |
|---|---|---|---|
| pGX0001 | 30 µg | 0.08 ± 0.07 | n/a |
| pGX1440 | 10 µg | 0.37 ± 0.23 | 0.097 |
|  | 20 µg | 0.30 ± 0.15 | 0.256 |
|  | 30 µg | 0.49 ± 0.20 | 0.012 |
|  | 50 µg | 0.50 ± 0.30 | 0.010 |

Statistical significance assumed at p 0.05. p-values reported are relative to naive (pGX0001 immunized mice)

Similar to the magnitude of antigen specific CD8 T cells, synthetic consensus BORIS antigen induced a significant change in the frequency of CD8+CD107a+ T cells among all groups compared to naïve (0.02%±0.01%) (FIG. 9C). Specifically, the frequency of antigen specific CD8+CD107a+ T cells was 11.52%±3.50%, 14.49%±5.22%, 13.57%±3.45%, and 16.24%±7.74% in the 10 µg (p=0.002), 20 µg (p<0.001), 30 µg (p<0.001), and 50 µg (p<0.001) dose groups, respectively (FIG. 9B). The cytokine profile of synthetic consensus BORIS antigen specific CD8+CD107a+ T cells was similar across dose groups and majority was comprised of IFNγ+IL-2−TNFα− with some IFNγ+IL-2−TNFα+ cells (FIG. 9D). The frequency of antigen specific CD8+ T cells with cytolytic potential is further detailed in Table 8.

TABLE 8

Cytolytic potential of antigen specific CD8+ T cells induced by synthetic consensus BORIS antigen
Synthetic consensus BORIS antigen CD8+CD107a+ T cells

| Construct | Dose | % CD8+CD107a+ ± Std. Dev. | p-value |
|---|---|---|---|
| pGX0001 | 30 µg | 0.02 ± 0.01 | n/a |
| pGX1440 | 10 µg | 11.52 ± 3.50 | 0.002 |
|  | 20 µg | 14.49 ± 5.22 | <0.001 |
|  | 30 µg | 13.57 ± 3.45 | <0.001 |
|  | 50 µg | 16.24 ± 7.74 | <0.001 |

Statistical significance assumed at p ≤ 0.05. p-values reported are relative to naive (pGX0001 immunized mice)

Overall there were no significant differences in responses between immunized groups for any data reported (i.e 10 µg was not significantly lower than 50 µg etc.). Synthetic consensus BORIS antigen significantly increased the frequency of antigen specific CD4+, CD4+CD107a+ and CD8+, CD8+CD107a+ T cells, compared to naïve, although the magnitude of the response was much more robust in the CD8+ T cell compartment.

What is claimed is:

1. A protein comprising:
   (a) amino acids 19-680 of SEQ ID NO:2;
   (b) at least 90% of an entire length of amino acids 19-680 of SEQ ID NO:2 at 100% sequence identity to SEQ ID NO: 2 and mutations C276G, C279G, C304G, C307G, C332G, C335G, C361G, C364G, C389G, C392G, C417G, C420G, C447G, C450G, C477G, C480G, C505G, C508G, C533G, C536G, C565G, C568G, and K603R of SEQ ID NO: 2;
   (c) an amino acid sequence that is at least 95% identical to amino acids 19-680 of SEQ ID NO:2 and mutations C276G, C279G, C304G, C307G, C332G, C335G, C361G, C364G, C389G, C392G, C417G, C420G, C447G, C450G, C477G, C480G, C505G, C508G, C533G, C536G, C565G, C568G, and K603R of SEQ ID NO: 2; or
   (d) at least 90% of an entire length of amino acid sequence that is at least 95% identical to amino acids 19-680 of SEQ ID NO:2 and mutations C276G, C279G, C304G, C307G, C332G, C335G, C361G, C364G, C389G, C392G, C417G, C420G, C447G, C450G, C477G, C480G, C505G, C508G, C533G, C536G, C565G, C568G, and K603R of SEQ ID NO: 2.

2. The protein of claim 1 comprising:
   (a) the amino acid sequence of SEQ ID NO:2;
   (b) at least 90% of an entire length of the amino acid sequence of SEQ ID NO:2 at 100% sequence identity to SEQ ID NO: 2 and mutations C276G, C279G, C304G, C307G, C332G, C335G, C361G, C364G, C389G, C392G, C417G, C420G, C447G, C450G, C477G, C480G, C505G, C508G, C533G, C536G, C565G, C568G, and K603R of SEQ ID NO: 2;

(c) an amino acid sequence that is at least 95% identical to the amino acid sequence of SEQ ID NO: 2 and mutations C276G, C279G, C304G, C307G, C332G, C335G, C361G, C364G, C389G, C392G, C417G, C420G, C447G, C450G, C477G, C480G, C505G, C508G, C533G, C536G, C565G, C568G, and K603R of SEQ ID NO: 2; or (d) at least 90% of an entire length of an amino acid sequence that is at least 95% identical to the amino acid sequence of SEQ ID NO:2 and mutations C276G, C279G, C304G, C307G, C332G, C335G, C361G, C364G, C389G, C392G, C417G, C420G, C447G, C450G, C477G, C480G, C505G, C508G, C533G, C536G, C565G, C568G, and K603R of SEQ ID NO: 2.

3. The protein of claim 2 comprising the amino acid sequence of SEQ ID NO:2.

\* \* \* \* \*

SEQUENCE LISTING

<160> NUMBER OF SEQ ID NOS: 2

<210> SEQ ID NO 1

<211> LENGTH: 2046
<212> TYPE: DNA
<213> ORGANISM: Artificial Sequence
<220> FEATURE:
<223> OTHER INFORMATION: Synthetic Consensus BORIS (CTCFL) DNA Coding
      Sequence pGX1440

<400> SEQUENCE: 1

| | | | | | | |
|---|---|---|---|---|---|---|
| atggattgga | cttggattct | gttcctggtc | gcagcagcaa | ctagagtgca | ttccgcagcc | 60 |
| accgagattt | ccgtcctgag | tgagcagttc | accaagatca | aggagctgga | gctgatgccc | 120 |
| gagaagggcc | tgaaggagga | ggagaaggac | ggcgtgtgca | gagagaagga | tcacaggtcc | 180 |
| ccttctgagc | tggaggccga | gagaacaagc | ggagcattcc | aggactccgt | gctggaggag | 240 |
| gaggtggagc | tggtgctggc | accatctgag | gagagcgaga | gcacatcct | gacactgcag | 300 |
| accgtgcact | ttacctctga | ggccgtggag | ctgcaggata | tgtccctgct | gtctatccag | 360 |
| cagcaggagg | gagtgcaggt | ggtggtgcag | cagccaggcc | ctggcctgct | gtggctggag | 420 |
| gagggaccta | gcagtccct | gcagcagtat | gtggccatct | ctatccagca | ggagctgtac | 480 |
| agcctgcagg | agatggaggt | gctgcagttt | cacgccctgg | aggagaatgt | gatggtggcc | 540 |
| agcgaggact | ccaagctggc | cgtgagcctg | cagagacag | caggcctgat | caagctggag | 600 |
| gagggccagg | agaagaacca | gctgctggcc | gagcgcacaa | aggagcagct | gttctttgtg | 660 |
| gagacaatgt | ctggcgacga | gcggagcgat | gagatcgtgc | tgacagtgag | caactccaat | 720 |
| gtggaggagc | aggaggacca | gccaaccgca | ggacaggccg | atgccgagaa | ggccaagtcc | 780 |
| acaaagaatc | agagaaagac | caagggcgcc | aagaggacat | tccacggcga | cgtgggcatg | 840 |
| tttacaagct | cccgcatgtc | tagcttcaac | cggcacatga | gacccacac | aaatgagaag | 900 |
| ccacacctgg | ccacctggg | cctgaagacc | tttagaaccg | tgacactgct | gaggaaccac | 960 |
| gtgaataccc | acacaggcac | cagaccctat | aagggcaacg | atggcaatat | ggccttcgtg | 1020 |
| acaagcggcg | agctggtgag | gcaccggaga | tataagcaca | cccacgagaa | gccttttaag | 1080 |
| ggctccatgg | gcaagtacgc | cagcgtggag | gcctccaagc | tgaagaggca | cgtgcggagc | 1140 |
| cacaccggag | agcggccctt | ccagggctgt | cagggctctt | acgccagcag | ggacacatat | 1200 |
| aagctgaaga | gacacatgag | gacccactct | ggcgagaagc | cctatgaggg | ccacatcggc | 1260 |
| cacacacgct | ttacccagag | cggcacaatg | aagatccaca | tcctgcagaa | gcacggcgag | 1320 |
| aatgtgccaa | gtaccaggg | accacacgga | gcaaccatca | tcgcacgaa | gtccgatctg | 1380 |
| cgcgtgcaca | tgaggaacct | gcacgcatac | agcgccgcag | agctgaaggg | cagatatggc | 1440 |
| tccgccgtgt | tccacgagag | gtacgccctg | atccagcacc | agaagacaca | caagaacgag | 1500 |
| aagcggttca | agggcaagca | cggcagctac | gcctgcaagc | aggagcgcca | catgacagcc | 1560 |
| cacatccgga | cacacaccgg | cgagaagcct | ttcaccggcc | tgtccggcaa | caagtgtttt | 1620 |
| cgccagaagc | agctgctgaa | tgcccacttc | cggaagtatc | acgacgccaa | ctttatccca | 1680 |
| accgtgtaca | agggctccaa | gggcggcaag | ggcttctctc | gctggatcaa | tctgcaccgg | 1740 |
| cactccgaga | gtgcggctc | tggagaggca | aagtccgccg | catctggcaa | gggcaggcgc | 1800 |
| acccggagaa | ggaagcagac | aatcctgaag | gaggcaacca | agggacagaa | ggaggcagca | 1860 |
| aagggatgga | aggaggcagc | aaacggcgat | gaggcagcag | ccgaggaggc | cagcaccaca | 1920 |
| aagggcgagc | agttccctgg | cgagatgttt | ccagtggcct | gtggcgagac | aacagccaga | 1980 |
| gtgaaggaag | aagtggatga | aggggtgacc | tgtgagatgc | tgctgaacat | gatggacaaa | 2040 |
| tgataa | | | | | | 2046 |

-continued

```
<210> SEQ ID NO 2
<211> LENGTH: 680
<212> TYPE: PRT
<213> ORGANISM: Artificial Sequence
<220> FEATURE:
<223> OTHER INFORMATION: Synthetic Consensus BORIS (CTCFL) Protein
      Sequence pGX1440

<400> SEQUENCE: 2

Met Asp Trp Thr Trp Ile Leu Phe Leu Val Ala Ala Thr Arg Val
1               5                   10                  15

His Ser Ala Ala Thr Glu Ile Ser Val Leu Ser Glu Gln Phe Thr Lys
                20                  25                  30

Ile Lys Glu Leu Glu Leu Met Pro Glu Lys Gly Leu Lys Glu Glu Glu
            35                  40                  45

Lys Asp Gly Val Cys Arg Glu Lys Asp His Arg Ser Pro Ser Glu Leu
50                  55                  60

Glu Ala Glu Arg Thr Ser Gly Ala Phe Gln Asp Ser Val Leu Glu Glu
65                  70                  75                  80

Glu Val Glu Leu Val Leu Ala Pro Ser Glu Glu Ser Glu Lys His Ile
                85                  90                  95

Leu Thr Leu Gln Thr Val His Phe Thr Ser Glu Ala Val Glu Leu Gln
                100                 105                 110

Asp Met Ser Leu Leu Ser Ile Gln Gln Gln Gly Val Gln Val Val
                115                 120                 125

Val Gln Gln Pro Gly Pro Gly Leu Leu Trp Leu Glu Glu Gly Pro Arg
130                 135                 140

Gln Ser Leu Gln Gln Tyr Val Ala Ile Ser Ile Gln Gln Glu Leu Tyr
145                 150                 155                 160

Ser Leu Gln Glu Met Glu Val Leu Gln Phe His Ala Leu Glu Glu Asn
                165                 170                 175

Val Met Val Ala Ser Glu Asp Ser Lys Leu Ala Val Ser Leu Ala Glu
                180                 185                 190

Thr Ala Gly Leu Ile Lys Leu Glu Glu Gly Gln Glu Lys Asn Gln Leu
                195                 200                 205

Leu Ala Glu Arg Thr Lys Glu Gln Leu Phe Phe Val Glu Thr Met Ser
210                 215                 220

Gly Asp Glu Arg Ser Asp Glu Ile Val Leu Thr Val Ser Asn Ser Asn
225                 230                 235                 240

Val Glu Glu Gln Glu Asp Gln Pro Thr Ala Gly Gln Ala Asp Ala Glu
                245                 250                 255

Lys Ala Lys Ser Thr Lys Asn Gln Arg Lys Thr Lys Gly Ala Lys Arg
                260                 265                 270

Thr Phe His Gly Asp Val Gly Met Phe Thr Ser Ser Arg Met Ser Ser
                275                 280                 285

Phe Asn Arg His Met Lys Thr His Thr Asn Glu Lys Pro His Leu Gly
                290                 295                 300

His Leu Gly Leu Lys Thr Phe Arg Thr Val Thr Leu Leu Arg Asn His
305                 310                 315                 320

Val Asn Thr His Thr Gly Thr Arg Pro Tyr Lys Gly Asn Asp Gly Asn
                325                 330                 335

Met Ala Phe Val Thr Ser Gly Glu Leu Val Arg His Arg Arg Tyr Lys
                340                 345                 350

His Thr His Glu Lys Pro Phe Lys Gly Ser Met Gly Lys Tyr Ala Ser
                355                 360                 365
```

```
Val Glu Ala Ser Lys Leu Lys Arg His Val Arg Ser His Thr Gly Glu
            370                 375                 380

Arg Pro Phe Gln Gly Cys Gln Gly Ser Tyr Ala Ser Arg Asp Thr Tyr
385                 390                 395                 400

Lys Leu Lys Arg His Met Arg Thr His Ser Gly Glu Lys Pro Tyr Glu
                405                 410                 415

Gly His Ile Gly His Thr Arg Phe Thr Gln Ser Gly Thr Met Lys Ile
                420                 425                 430

His Ile Leu Gln Lys His Gly Glu Asn Val Pro Lys Tyr Gln Gly Pro
            435                 440                 445

His Gly Ala Thr Ile Ile Ala Arg Lys Ser Asp Leu Arg Val His Met
450                 455                 460

Arg Asn Leu His Ala Tyr Ser Ala Ala Glu Leu Lys Gly Arg Tyr Gly
465                 470                 475                 480

Ser Ala Val Phe His Glu Arg Tyr Ala Leu Ile Gln His Gln Lys Thr
                485                 490                 495

His Lys Asn Glu Lys Arg Phe Lys Gly Lys His Gly Ser Tyr Ala Cys
            500                 505                 510

Lys Gln Glu Arg His Met Thr Ala His Ile Arg Thr His Thr Gly Glu
            515                 520                 525

Lys Pro Phe Thr Gly Leu Ser Gly Asn Lys Cys Phe Arg Gln Lys Gln
            530                 535                 540

Leu Leu Asn Ala His Phe Arg Lys Tyr His Asp Ala Asn Phe Ile Pro
545                 550                 555                 560

Thr Val Tyr Lys Gly Ser Lys Gly Lys Gly Lys Phe Ser Arg Trp Ile
                565                 570                 575

Asn Leu His Arg His Ser Glu Lys Cys Gly Ser Gly Glu Ala Lys Ser
            580                 585                 590

Ala Ala Ser Gly Lys Gly Arg Arg Thr Arg Arg Lys Gln Thr Ile
            595                 600                 605

Leu Lys Glu Ala Thr Lys Gly Gln Lys Glu Ala Ala Lys Gly Trp Lys
610                 615                 620

Glu Ala Ala Asn Gly Asp Glu Ala Ala Glu Glu Ala Ser Thr Thr
625                 630                 635                 640

Lys Gly Glu Gln Phe Pro Gly Glu Met Phe Pro Val Ala Cys Gly Glu
                645                 650                 655

Thr Thr Ala Arg Val Lys Glu Glu Val Asp Glu Gly Val Thr Cys Glu
                660                 665                 670

Met Leu Leu Asn Met Met Asp Lys
            675                 680
```